(12) United States Patent
Khalil et al.

(10) Patent No.: US 6,615,061 B1
(45) Date of Patent: Sep. 2, 2003

(54) OPTICAL SENSOR HAVING A SELECTABLE SAMPLING DISTANCE FOR DETERMINATION OF ANALYTES

(75) Inventors: Omar S. Khalil, Libertyville; Xiaomao Wu, Gurnee; Shu-jen Yeh, Grayslake; Charles F. Hanna, Libertyville; Stanislaw Kantor, Buffalo Grove; Tzyy-Wen Jeng, Vernon Hills, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/366,084

(22) Filed: Aug. 3, 1999

Related U.S. Application Data

(63) Continuation-in-part of application No. 09/198,094, filed on Nov. 23, 1998, now Pat. No. 6,121,566.

(51) Int. Cl.[7] .............................................. A61B 5/00
(52) U.S. Cl. ...................... 600/310; 600/316; 600/331
(58) Field of Search ................................ 600/310, 316, 600/322, 323, 326, 331, 365, 473, 476

(56) References Cited

U.S. PATENT DOCUMENTS

| | | |
|---|---|---|
| 3,638,640 A | 2/1972 | Shaw |
| 4,223,680 A | 9/1980 | Jobsis |
| 4,655,225 A | 4/1987 | Dähne et al. |
| 5,007,423 A | 4/1991 | Branstetter et al. |
| 5,057,695 A | 10/1991 | Hirao et al. |
| 5,086,229 A | 2/1992 | Rosenthal et al. |
| 5,122,974 A | 6/1992 | Chance |
| 5,187,672 A | 2/1993 | Chance et al. |
| 5,237,178 A | 8/1993 | Rosenthal et al. |

(List continued on next page.)

FOREIGN PATENT DOCUMENTS

| | | |
|---|---|---|
| EP | 0 627 619 | 12/1994 |
| EP | 0 843 986 | 5/1998 |
| WO | 9220273 | 11/1992 |
| WO | 9313706 | 7/1993 |
| WO | 97/27800 | 8/1997 |
| WO | 99/39631 | 8/1999 |

OTHER PUBLICATIONS

Tooke et al., "Skin Microvascular Blood Flow Control in Long Duration Diabetics with and Without Complications", Diabetes Research (1987) 5, 189–192.

(List continued on next page.)

*Primary Examiner*—Eric F. Winakur
(74) *Attorney, Agent, or Firm*—David L. Weinstein

(57) ABSTRACT

A method and apparatus for the measurement of transcutaneous diffuse reflectance at a single sampling distance for determining the concentration of an analyte in a biological sample, such as, for example, human tissue. The determination of the concentration of the analyte has been found to depend on the sampling distance and reaches an optimal result at a defined sampling distance for a given analyte and a given sample. The method involves measuring the light re-emitted from the sample at a distance from a light introduction site and correlating the intensity of the re-emitted light to the concentration of an analyte. For a given sample, the distance between the light collection site and a light introduction site (i.e., the sampling distance) corresponds to the depth from the surface into the sample at which scattering and absorption events significantly affect the intensity of re-emitted light (i.e., the sampling depth). Prior knowledge about the sample determines the optimal sampling depth for performing a measurement for a specific analyte and the corresponding sampling distance needed to reach that optimal sampling depth. Optimization of the sampling distance, as well as the correlation relationship, can be established in a calibration procedure.

70 Claims, 9 Drawing Sheets

U.S. PATENT DOCUMENTS

| | | | |
|---|---|---|---|
| 5,277,181 A | 1/1994 | Mendelson et al. | |
| 5,297,548 A | 3/1994 | Pologe | |
| 5,324,979 A | 6/1994 | Rosenthal | |
| 5,372,136 A | 12/1994 | Steuer et al. | |
| 5,419,321 A | 5/1995 | Evans | |
| 5,490,506 A | 2/1996 | Takatani et al. | |
| 5,492,118 A | 2/1996 | Gratton et al. | |
| 5,492,769 A | 2/1996 | Pryor et al. | |
| 5,499,627 A | 3/1996 | Steuer et al. | |
| 5,513,642 A | 5/1996 | Ostrander | |
| 5,524,617 A | 6/1996 | Mannheimer | |
| 5,551,422 A | 9/1996 | Simonsen et al. | |
| 5,553,615 A | 9/1996 | Carim et al. | |
| 5,632,273 A | 5/1997 | Suzuki | |
| 5,676,143 A | 10/1997 | Simonsen et al. | |
| 5,720,284 A | 2/1998 | Aoyagi et al. | |
| 5,725,480 A | 3/1998 | Oosta et al. | |
| 5,770,454 A | 6/1998 | Essenpreis et al. | |
| 5,844,239 A | 12/1998 | Kimura | |
| 5,902,235 A | * 5/1999 | Lewis et al. | 600/323 |

OTHER PUBLICATIONS

S.L. Robbins et al., *Pathologic Basis of Disease*, 3$^{rd}$ Edition, W.B. Saunders Company, Philadelphia, 1984, p. 972–990.

G. S. Wilson et al., "Progress toward the Development of an Implantable Sensor for Glucose", Clin. Chem. 38/9, 1613–1617 (1992).

L. Reynolds et al., "Diffuse reflectance from a finite blood medium: applications to the modeling of fiber optic catheters", Applied Optics, vol. 15, No. 9 (1976), pp. 2059–2067.

R. A. J. Groenhuis et al., "Scattering and absorption of turbid materials determined from reflection measurements. 1: Theory", Applied Optics, vol. 22, No. 16 (1983), pp. 2456–2462.

M.S. Patterson et al., "Quantitative reflectance spectrophotometry for the noninvasive measurement of photosensitizer concentration in tissue during photodynamic therapy", SPIE (Society for Photo–optical Instrument Engineering) Proceedings, vol. 1065 (1989), pp. 115–122.

B. Chance et al., "Effects of Solutes on Optical Properties of Biological Materials: Models, Cells, and Tissues", Analytical Biochemistry, 227, 351–362 (1995).

H. Liu et al., "Dependence of Tissue Optical Properties on Solute–Induced Changes in Refractive Index and Osmolarity", Journal of Biomedical Optics, vol. 1, No. 2, 200–211 (Apr. 1996).

J. Que et al., "Monte Carlo Modelings Studies of the Effect Of Physiological Factors and Other Analytes on the Determination of Glucose Concentration in vivo by Near Infrared Optical Absorption and Scattering Measurements", Journal of Biomedical Optics 2(3), 319–325 (Jul. 1997).

I.M. Braverman, "The Cutaneous Microcirculation: Ultrastructure and Microanatomical Organization", Microcirculation, vol. 4, No. 3 (1997) pp. 329–340.

G. Kumar et al., "Optical probe geometry for near–infrared spectroscopy of biological tissue", Applied Optics, vol. 36, No. 10 (Apr. 1, 1997), pp. 2286–2293.

W. Steenbergen et al., "New optical tissue phantom, and its use for studying laser Doppler blood flowmetry", SPIE Proceedings, vol. 3196 (1997), pp. 12–23.

R. Graaff et al., "Reduced light–scattering properties for mixtures of spherical particles: a simple approximation derived from Mie calculations", Applied Optics, vol. 31, No. 10 (Apr. 1, 1992), pp. 1370–1376.

Tsuchiya, Y, et al., "Quantitation of absorbing substances in turbid media such a human tissues based on the microscopic Beer–Lambert law", Optics Communications, NL, North–Holland Publishing Co., vol. 144, No. 4–6 (1997) pp. 269–280.

Wilson, B. et al., "Optical Reflectance and Transmittance of Tissues: Principles and Applications", IEEE Journal of Quantum Electronics, US, IEEE Inc., New York, vol. 26, No. 12, (1990) pp 2186–2199.

* cited by examiner

OPTICAL SENSOR HAVING A SELECTABLE SAMPLING DISTANCE FOR DETERMINATION OF ANALYTES

This application is a continuation-in-part of U.S. Ser. No. 09/198,094, filed Nov. 23, 1998 now U.S. Pat. No. 6,121,566.

BACKGROUND OF THE INVENTION

1. Field of the Invention

This invention relates to devices and methods for the determination of the concentration of an analyte in a human tissue. More specifically, this invention relates to devices and methods for the non-invasive determination of the concentration of one or more analytes in vivo in a human tissue, wherein an optical property at a given depth in the tissue is significantly affected by a given analyte.

2. Discussion of the Art

Non-invasive monitoring of analytes in the human body by optical devices and methods is an important tool for clinical diagnosis. "Non-invasive" (alternatively referred to herein as "NI") monitoring techniques measure in vivo concentrations of analytes in the blood without taking out a blood sample from the human body. As defined herein, a "non-invasive" technique is one that can be used without removing a sample from, or without inserting any instrumentation into, the human body. The ability to determine an analyte, or a disease state, in a human subject without performing an invasive procedure, such as removing a sample of blood or a biopsy specimen, has several advantages. These advantages include ease in performing the test, reduced pain and discomfort to the patient, and decreased exposure to potential biohazards. These advantages will promote increased frequency of testing, accurate monitoring and control of a disease condition, and improved patient care. Representative examples of non-invasive monitoring techniques include pulse oximetry for oxygen saturation (U.S. Pat. Nos. 3,638,640; 4,223,680; 5,007,423; 5,277,181; 5,297,548). Another example is the use of laser Doppler flowmetry for diagnosis of circulation disorders (Tooke et al, "Skin microvascular blood flow control in long duration diabetics with and without complication", Diabetes Research, Vol. 5, 1987, pages 189–192). Other examples of NI techniques include determination of tissue oxygenation (WO 92/20273), determination of hemoglobin (U.S. Pat. No. 5,720,284), and hematocrit (U.S. Pat. Nos. 5,553,615; 5,372,136; 5,499,627; WO 93/13706). Determination of bilirubin was also described in the art (R. E. Schumacher, "Noninvasive measurement of bilirubin in the newborn", Clinics in Perinatology, Volume 17, 1990, pages 417–435, and U.S. Pat. No. 5,353,790).

Measurements in the near-infrared region of the electromagnetic spectrum have been proposed, or used, in the prior art. The 600 nm to 1300 nm region of the electromagnetic spectrum represents a window between the visible hemoglobin and melanin absorption bands and the strong infrared water absorption bands. Light having a wavelength of 600 nm to 1300 nm can penetrate sufficiently deep into the skin to allow use thereof in a spectral measurement or a therapeutic procedure.

Oximetry measurement is very important for critical patient care, especially after the use of anesthesia. Oxygenation measurements of tissue are also important diagnostic tools for measuring oxygen content of the brain of the newborn during and after delivery, for monitoring tissue healing, and in sports medicine.

Non-invasive determination of hemoglobin and hematocrit values in blood would offer a simple, non-biohazardous, painless procedure for use in blood donation centers. Such techniques could increase the number of donations by offering an alternative to an invasive procedure, which is inaccurate and may possibly lead to the rejection of a number of qualified donors. Non-invasive determination of hemoglobin and hematocrit values would be useful for the diagnosis of anemia in infants and mothers, without the pain associated with blood sampling. Non-invasive determination of hemoglobin has been considered as a method for localizing tumors and diagnosis of hematoma and internal bleeding (S. Gopinath, et al., "Near-infrared spectroscopic localization of intracamerial hematomas", J. Neurosurgery, Vol. 79, 1993, pages 43–47). Non-invasive determination of hematocrit values can yield important diagnostic information on patients with kidney failure before and during dialysis (R. R. Steuer, et al., "A new optical technique for monitoring hematocrit and circulating blood volume; Its application in renal dialysis", Dialysis and Transplantation, Volume 22, 1993, pages 260–265). There are more than 50 million dialysis procedures performed in the United States and close to 80 million dialysis procedures performed world-wide annually.

Non-invasive diagnosis and monitoring of diabetes may be the most important potential advantage for non-invasive diagnostics. Diabetes mellitus is a chronic disorder of carbohydrate, fat, and protein metabolism characterized by an absolute or relative insulin deficiency, hyperglycemia, and glycosuria. At least two major variants of the disease have been identified. "Type I" accounts for about 10% of diabetics and is characterized by a severe insulin deficiency resulting from a loss of insulin-secreting beta cells in the pancreas. The remainder of diabetic patients suffer from "Type II", which is characterized by an impaired insulin response in the peripheral tissues (Robbins, S. L. et al., *Pathologic Basis of Disease*, 3rd Edition, W. B. Saunders Company, Philadelphia, 1984, p. 972). If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

The concept upon which most NI detection procedures are based involves irradiating a tissue or a vascular region of the body with electromagnetic radiation and measuring the spectral information that results from at least one of three primary processes: absorption, scattering, and emission. The extent to which each of these processes occurs is dependent upon a variety of factors, including the wavelength of the incident radiation and the concentration of analytes in the body part. Signals are measured as a change in reflectance or transmittance of the body part. Concentration of an analyte, e.g., glucose, hemoglobin or bilirubin is determined from the spectral information by comparing the measured spectra to a calibration data set. Alternatively the concentration of an analyte is determined by comparing the magnitude of the change in signal to the results of calculations based on a physical model describing the optical properties of the tissue under examination. Various categories of non-invasive measurement techniques will now be described.

NI techniques that utilize the interaction of a sample with infrared radiation can be categorized according to three distinct wavelength regions of the electromagnetic spectrum: near-infrared (NIR), mid-infrared (MIR) and far-infrared (FIR). As defined herein, NIR involves the wavelength range from about 600 nm to about 1300 nm, MIR involves the wavelength range from about 1300 nm to about 3000 nm, and FIR involves the wavelength range from about 3000 nm to about 25000 nm. As defined herein, "infrared" (or IR) is taken to mean a range of wavelengths from about 600 nm to about 25000 nm.

Due to the highly scattering and absorption nature of the human skin and tissue, light in the 600 nm to 1300 nm spectral range penetrates the skin and underlying tissues to different depths. The tissue depth at which most of the reflectance signal is generated (sampling depth) depends on the wavelength of light and positioning of the source and detector. Analyzing the reflected or transmitted signal without accounting for the effect of different layers of skin can lead to erroneous estimates of the optical properties of the tissue and hence, the concentration of metabolites determined from these measured properties. The stratum corneum, epidermis, dermis, adipose tissue, and muscle layers can interact with light differently and contribute separately to the measured signals. Controlling the sampling depth of the light and understanding the effect of the different layers of the skin on the generated signal are important for the accurate non-invasive determination of metabolites in tissues. The NIR spectral region has been used for determination of blood oxygen saturation, bilirubin, hemoglobin, hematocrit, and tissue fat content. It is also used for exciting and detecting therapeutic agents in photodynamic therapy. At longer wavelengths in MIR region, water absorption bands are dominant in tissue spectra. There are some narrower spectral windows in the 1500 nm to 1900 nm range and the 2100 nm to 2500 nm range, where both in vitro and in vivo tissue measurements have been performed.

Light striking a tissue will undergo absorption and scattering. Most of the scattered photons are elastically scattered, i.e., they keep the same frequency as the incident radiation (e.g., Rayleigh scattering). A small fraction of the scattered light (less than one in a thousand incident photons) is inelastically scattered (Raman scattering). Unless otherwise indicated herein, "scattering" refers to elastic scattering.

Because of the multiple scattering effect of tissue, optical measurements of either transmission or reflectance will contain tissue scattering information, as well as absorption information. Tissue scattering information includes cell size and cell shape, depth of the tissue layer in which scattering occurs, and refractive index of intracellular fluids and extracellular fluid (interstitial fluid). Absorption information includes absorption by tissue components, such as hemoglobin, melanin, and bilirubin, and the overtone absorption of water, glucose, lipids, and other metabolites.

One method for measuring elastic light scattering of tissues and turbid media is spatially resolved diffuse reflectance (SRDR), where detection fibers are placed at multiple distances from a light entry point. Reflectance values at different distances from the illumination point are used to calculate the absorption and scattering coefficients of the tissue based on photon diffusion theory models or numerical calculations such as Monte Carlo simulations. The values of the absorption and scattering coefficients are then used to correlate with the concentration of an analyte.

As shown in FIG. 1, light is introduced into the surface of a tissue sample, such as a body part, at an introduction site. The diffusely reflected light is measured at two or more detection sites located on the surface of the sample (e.g., the skin) at different distances, r, from the introduction site. The dependence of the intensity of the diffusely reflected light, i.e., reflectance R, as a function of the distance between the detector and the light source in touch with the sample (r) is used to derive scattering and absorption coefficients of the tissue sample. These coefficients, in turn, are correlated with the concentration of analyte(s) (see, for example, U.S. Pat. No. 5,492,118).

European Patent No. 0843986A2 describes a reflectance spectrophotometer for blood glucose measurement from human skin. The spectrophotometer intends to minimize the influence of undesirable spectral information from the epidermis by separating the light introduction site and the light detection site. This undesirable spectral information is in the form of diffuse surface reflectance that depends on the condition of the surface of the skin. In the arrangement disclosed therein, however, light penetrates through the epidermis twice—once at the light introduction site and once at the light detection site, and its properties will be affected by the optical properties of the epidermis. The method of European Patent No. 0843986A2 is based on the erroneous assumption that light penetrating to a lower layer of the skin will not be affected by the optical properties of the upper layers. The method does not account for both of the scattering and absorption properties of different skin layers being affected by different tissue analytes and relies mainly on absorption of glucose in the 1300–2500 spectral range, which is dominated mainly by water absorption.

The above prior art methods do not address the effect of skin layers on signal, distribution of analytes in these layers, and the effect of each analyte on the optical properties of each layer.

The use of absorption and scattering coefficients derived from mathematical models that assume homogeneous non-layered structures can lead to inaccurate determination of analytes in tissue. Further, use of measurement methods that average out over several layers and multiple compartments of the skin or other samples can also lead to complicated and misrepresenting data.

An important variable in an in vivo measurement is the fluctuation of blood volume at the measurement site. Fluctuation in blood volume at the measurement site could result from such factors as lack of anatomical homogeneity, blood vessel dilation or constriction due to hormonal control, or change in ambient temperature. A change in the volume fraction of the blood can lead to erroneous measurement if the concentration of a non-absorbing analyte is calculated from scattering data as suggested by U.S. Pat. Nos. 5,551, 422 and 5,492,118. Scattering of red blood cells and the effect of blood volume on fluid contents of tissue affect the values of the scattering coefficients and hence the calculated concentration of analytes such as glucose determined in the near-IR (600-nm to1300 nm). In the same manner, changes in scattering values of tissue affect the calculated values of the absorption coefficient and can affect the calculated concentrations of absorbing analytes, such as hemoglobin, bilirubin, and colored therapeutic agents.

Although a variety of techniques have been disclosed in the art, there is still no commercially available device that provides non-invasive glucose measurements with an accuracy that is comparable to the established invasive methods. Devices for non-invasive measurement of bilirubin and hematocrit have been commercialized. However, signals obtained by prior art methods operate on the assumption that the tissue comprises a single uniform layer. As the change in optical signal due to a weakly absorbing analyte such as glucose is expected to be small, any approximation in the over-simplified skin model or in the calculation of the scattering and absorption coefficients will lead to erroneous results. The signals, for example, are vulnerable to the effects of top layers of the skin, which are significantly different from the deeper layers of the skin in terms of textures, colors, and other properties.

Thus, there is a continuing need for improved NI instruments and methods that are unaffected by variations in skin structures and layers or account for the effect of skin layers. There is also a need for instruments with simple calibration schemes that can be set in the factory and periodically checked for accuracy in the field.

Co-pending U.S. application Ser. No. 09/198,049, filed Nov. 23, 1998 ("Non-invasive sensor capable of determining optical parameters in a sample having multiple layers"), assigned to the assignee of this application, describes methods for determining optical properties of tissue with multiple layers. The methods involve the use of multiple groups of closely spaced optical fibers that are located at spatially resolved measurement sites. Each group yields information on a specific layer in the sample that is determined by the distance between the light illumination site and the residing site of the group. The layers described in the co-pending application are within the depth of 3 mm for human tissue samples. In body parts with a thin skin such as the forearm or the abdomen, this depth encompasses the stratum corneum, the epidermis and the dermis layers.

Skin components affect its optical properties in different ways depending if they are strongly absorbing, such as hemoglobin, bilirubin and melanin, or strongly scattering such as cells and muscle fibers. The color of the human skin is affected mostly by the contents of hemoglobin, melanin and bilirubin. Densities, sizes and shapes of cells and the refractive indexes of intercellular fluids (interstitial fluid) and intracellular fluid will affect skin scattering, especially in the relatively uniform epidermis and upper dermis. Analytes that may cause changes in the cell sizes and shapes and the refractive indexes of fluids can be tracked by measuring the scattering coefficient of these layers. Compounds that may have significant effect on these changes in the interstitial fluid are glucose, salts, proteins, fatty acids, and water. However, as light gets deeper into the dermis it starts to probe capillary beds and upper and lower plexus. Further deeper in the subcutaneous tissues, light interacts with capillaries, veins, various corpuscles, adipose tissues, etc.

SUMMARY OF THE INVENTION

We have discovered that the measurement of transcutaneous diffuse reflectance at a single sampling distance can achieve good correlation with the concentration of an analyte in a biological sample, such as, for example, human tissue. Such correlation has been found to depend on the sampling distance and reaches an optimal result at a defined sampling distance for a given analyte and a given biological sample.

This invention provides a method for determining the concentration of an analyte in a biological sample, typically one having a plurality of layers, e.g., a sample of human tissue. The method comprises the steps of:

(a) introducing a beam of light into the biological sample at a light introduction site on a surface of the biological sample;

(b) collecting the light re-emitted from the biological sample at a light collection site on the surface of the biological sample, the light collection site located at a distance from the light introduction site, the distance of the light collection site from the light introduction site corresponding to a sampling depth in the biological sample, at which sampling depth an optical property of the biological sample is significantly affected by the analyte;

(c) determining the intensity of the collected light; and (d) determining the concentration of the analyte from the intensity of the collected light.

The method involves measuring the light re-emitted at a distance from the light introduction site and correlating the intensity of the re-emitted light to the concentration of an analyte. For a given biological sample, the distance between the light collection site and a light introduction site (i.e., sampling distance) corresponds to the depth from the surface into the biological sample at which scattering and absorption events significantly affect the intensity of re-emitted light (i.e., sampling depth). Prior knowledge about the biological sample determines the optimal sampling depth for performing a measurement for a specific analyte and the corresponding sampling distance needed to reach that optimal sampling depth. Optimization of the sampling distance, as well as the correlation relationship, can be established in a calibration procedure described herein.

In a preferred embodiment of this invention, a method for determining the concentrations of a plurality of analytes in a biological sample, typically one having a plurality of layers, e.g., a sample of human tissue, comprises the steps of:

(a) introducing a beam of light into the biological sample at a light introduction site on a surface of the biological sample;

(b) collecting the light re-emitted from the biological sample at a light collection site on the surface of the biological sample, the light collection site located at a distance from the light introduction site, the distance of the light collection site from the light introduction site corresponding to a sampling depth in the biological sample, at which depth an optical property of the biological sample is significantly affected by one analyte of the plurality of analytes;

(c) determining the intensity of the collected light;

(d) determining the concentration of the one analyte of the plurality of analytes from the intensity of the collected light; and (e) repeating steps (a), (b), (c), and (d) for at least another analyte of the plurality of analytes.

The method of this invention is applicable for an arrangement wherein a single light introduction site and one or more light collection sites are employed. The method of this invention is also applicable for an arrangement wherein a single light collection site and one or more light introduction sites are employed. In either variation, the method is capable of determining the concentration of at least one component of a sample of human tissue having a plurality of layers, wherein each of these layers has different properties that are affected differently by the concentration of analytes in the tissue.

Another aspect of this invention involves a method whereby the selection of the sampling distance at which each analyte is determined is accomplished automatically by means of a programmable device. At the time of measurement, the sampling distance and the wavelength(s) of the incident light are selected by a computer, based on an input that includes the specific analyte to be determined and the prior knowledge about the sample.

In another aspect, this invention provides an apparatus for determining the concentration of at least one analyte in a biological sample, typically one having a plurality of layers, e.g., a sample of human tissue. The apparatus comprises:

(a) a means for introducing a beam of light into the biological sample at a light introduction site on a surface of the biological sample;

(b) a means for collecting light re-emitted from the biological sample at at least one light collection site on the surface, the at least one light collection site located at a predetermined sampling distance from the light introduction site, the predetermined sampling distance corresponding to a sampling depth, at which sampling depth an optical property of the biological sample is significantly affected by the analyte;

(c) a means for determining the intensity of the light collected at each light collection site; and (d) a means for determining the concentration of the at least one analyte from the intensity of the light collected at one of the light collection sites.

In an alternative of this apparatus, the apparatus comprises:

(a) a means for introducing a beam of light into the biological sample at at least one light introduction site on a surface of the biological sample;

(b) a means for collecting the light re-emitted from the biological sample at a light collection site on the surface, the at least one light introduction site being located at a predetermined distance, as measured on the surface, from the light collection site, each predetermined distance corresponding to a predetermined sampling depth in the biological sample;

(c) a means for determining the intensity of the light collected at the light collection site; and (d) a means for determining the concentration of at least one analyte from the intensity of the light collected at the light collection site.

In another aspect, a non-stationary illumination and detection system can be used and the sampling distance can be selected by moving a single illuminating element on the skin surface via a mechanism similar to a compact disk (CD) player read head. With a single light collecting element fixed at a given light collection site, the illuminating element can be moved to a predetermined position and thereby illuminate a site on the skin surface that is at a desired distance from the light collection site. Mechanisms for directing a light beam to predetermined sampling distances include beam steering devices such as moving mirrors or prisms. Alternatively, a system can comprise a stationary illuminating element and a movable light collection element.

This invention provides the following advantages over techniques that use a spatially resolved diffuse reflectance measurement (U.S. Pat. Nos. 5,075,695; 5,492,118; and 5,551,422):

(1) This invention accounts for the effect of the layers of tissue samples on the measurement.

(2) Selection of sampling distance, and, hence sampling depth, allows collection of optimal analyte signal relative to interfering signal for each analyte and each individual.

(3) This invention incorporates both absorption and scattering information and allocates appropriate balance between both types of information to maximize the effectiveness of analyte determination.

(4) In the normal mode of operation of this invention, signal detection relies on measurement at only one sampling distance, thereby simplifying the instrumentation.

(5) The method of this invention directly correlates the intensity of light collected to the concentration of an analyte and consequently eliminates the need for an algorithm for handling results based on assumptions such as the diffusion theory approximation or the complex Monte Carlo modeling computation. This invention also eliminates the errors associated with the conversion of reflectance values to scattering and absorption coefficients through empirical or semi-empirical algorithms.

DETAILED DESCRIPTION

Figure 1:
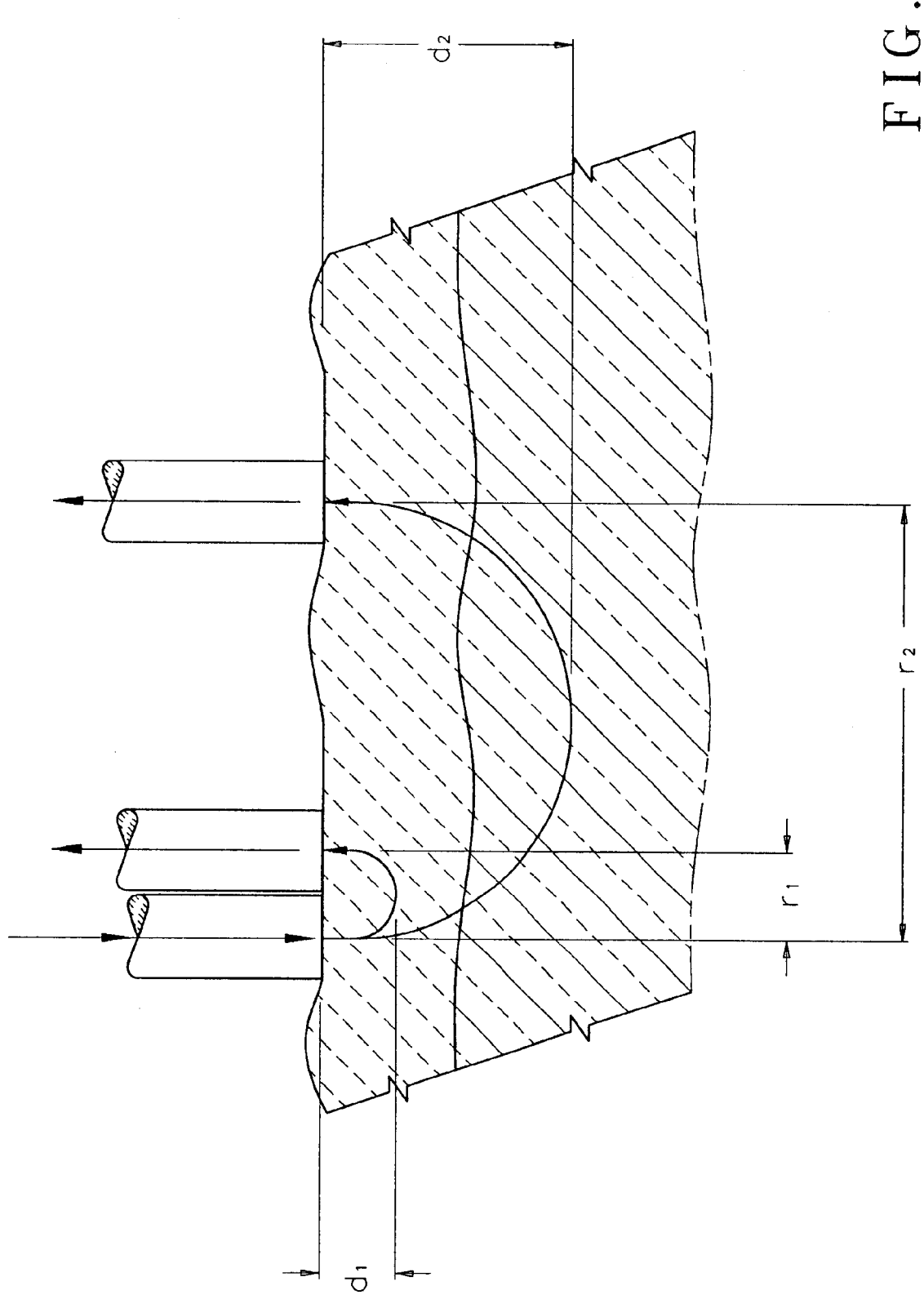
FIG. 1 is a schematic diagram illustrating (1) an arrangement of light collection sites with respect to the light introduction site and (2) the sampling depth, d, for a given sampling distance, r.

As used herein, "biological sample" includes, but is not limited to, a sample of intact or excised human tissue, such as, for example, a sample of intact or excised human skin, a human body part. Due to biological activities, the concentrations of components of a given biological sample may change over time. Repeated in vivo measurements of the biological sample may be required to monitor such changes. The expression "tissue optics" refers to the study of light propagation in biological tissues. The expression "optical properties" refers to the absorption, scattering, emission, and depolarization properties of the tissues. The expression "optical parameter" refers to a parameter that describes and defines an optical property of a medium and its components. Examples of optical parameters include absorption coefficients, scattering coefficients, anisotropy factors, transport optical mean free path, extinction coefficients of analytes. The expression "scattering media" refers to media that both scatter light and absorb light. The expression "absorption coefficient" (i.e., $\mu_a$) refers to the probability of light absorption per unit path length. The expression "scattering coefficient" (i.e., $\mu_s$) refers to the probability of light scattering per unit path length. The expression "anisotropy factor" (i.e., g) refers to the average cosine of the scattering angle for a multiply scattered photon. The expression "reduced scattering coefficient" (i.e., $\mu_s'$) refers to the probability of equivalently isotropic (uniform in all directions) scattering per unit path length. The reduced scattering coefficient is related to the scattering coefficient $\mu_s$ and the anisotropy factor g by the relationship $\mu_s'=(1-g)\mu_s$. The expression "penetration depth" (i.e., δ) refers to the rate of decay of light intensity in scattering media with respect to the path traveled by the light in the same direction as the incident light. Penetration depth δ is the reciprocal of the effective attenuation coefficient $\mu_{eff}$, i.e., $\delta=1/\mu_{eff}$. The expression "Monte Carlo simulation" refers to a numerical method that can be used to statistically describe photon propagation in scattering media. The expression "diffuse reflectance" (reflectance therein unless specified otherwise) refers to measurement of light that is re-emitted from a sample at all angles different from the direction of the incident light, and over an area wider than the area where the incident light is introduced into the sample. The expressions "spatially resolved scattering" or "spatially resolved diffuse reflectance" refer to a measurement of light that is re-emitted from a sample and collected at several light collection sites at specific distances from a light introduction site. Alternatively, these expressions can refer to the light collected at a given light collection site on the sample boundary as a result of introducing light at discrete light introduction sites located on the same boundary at defined distances from the light collection site. In both instances, $\mu_{eff}$, $\mu_a$ and $\mu_s'$ are calculated from the intensity distribution of the re-emitted light with respect to distances, i.e., the re-emitted light intensity at a multiplicity of sampling distances. The expressions "re-emitted light" and "reflected light" are used synonymously herein, as are the expressions "reflectance" and the "intensity of re-emitted light", unless otherwise indicated. The expression "frequency domain measurement" refers to a measurement of light involving the phase angle and/or the amplitude change of modulated incident light, at a given separation distance of a light introduction site from a light collection site, as the light transverses a scattering medium. The expression "beam of light" refers to a group of photons traveling together in nearly parallel trajectories toward a sample and striking the surface of the sample in a predefined area only. As a practical matter, the predefined area on the surface of a sample struck by a given beam of light is that area that is covered by an illuminating element, such as an optical fiber. The expression "significantly affect" refers to a measurable effect on an optical property of a biological sample at a given depth in that biological sample resulting from a change in concentration of an analyte at that depth. For example, in a sample of human skin, a change in concentration of melanine significantly affects the absorption coefficient in the epidermis. As another example, a change in concentration of hemoglobin significantly affects the absorption coefficient in the dermis and a change in concentration of glucose significantly affects the scattering coefficient in the epidermis and the dermis.

The expression "light introduction site" means a location on the surface of a sample, e.g., a body part, tissue, or the like, at which light is injected or inserted into the sample. The source of the light can be located at the light introduction site or can be located remote from the light introduction site. If the source of light is located remote from the light introduction site, the light must be transmitted to the light introduction site by light transmitting means, such as, for example, optical fibers. The expression "illuminating element" means a component located at the light introduction site that delivers light to the sample, e.g., a body part, tissue, or the like. The illuminating element is typically an optical fiber that transmits light from a source of light to the light introduction site. However, if the source of light is located at the light introduction site, the source of light can be the illuminating element. The expression "light collection site" means a location on the surface of a sample, e.g., a body part, tissue, or the like, at which light that is re-emitted from the sample is collected for measurement. The detector, which determines the intensity of the re-emitted light, can be located at the light collection site or can be located remote from the light collection site. If the detector is located remote from the light collection site, the light must be transmitted to the detector by light transmitting means, such as, for example, optical fibers. The expression "light collecting element" means a component located at the light collection site that collects light that is re-emitted from the sample, e.g., a body part, tissue, or the like. The light collecting element is typically an optical fiber that transmits light from the light collection site to a detector. However, if the detector can be located at the light collection site, the detector can be the light collecting element. The distance between a light introduction site and a light collection site, as measured along the surface of a sample, is defined as the "sampling distance". For a given sample, the sampling distance determines the mean depth from the surface of the sample into the interior of the sample from which the scattering and absorption events contribute to the measured re-emitted light. Such mean depth is hereinafter referred to as the "sampling depth", which is dependent on the sampling distance.

Figure 2:
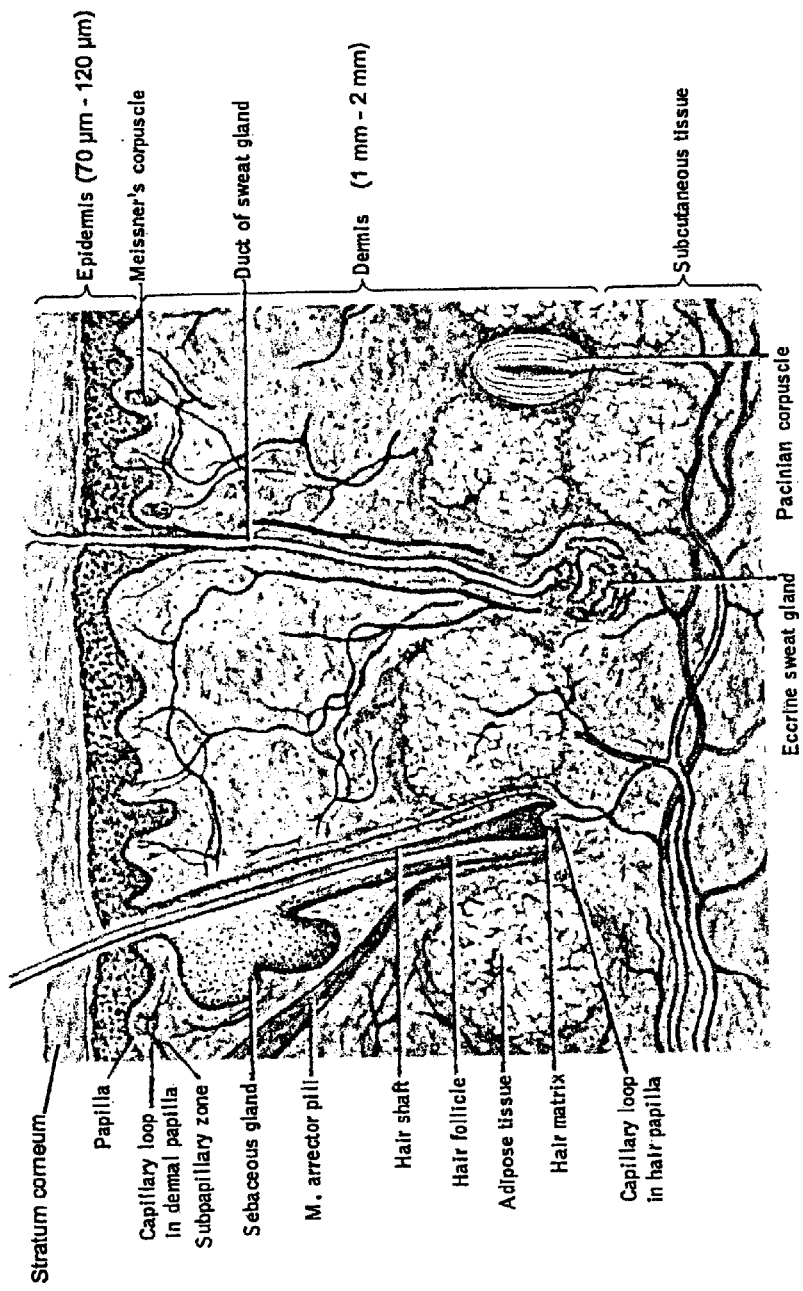
FIG. 2 is a diagram illustrating the layers of tissues in the skin.

A typical skin tissue of a human body is illustrated in FIG. 2 (Source: *Dorland's Illustrated Medical Dictionary*, 26th Ed., W. B. Saunders, Philadelphia, 1985, p. 1212). It is clearly shown that there are at least three identifiable layers of tissue in the skin, which are the epidermis, the dermis and subcutaneous tissue. The epidermis is the outermost and nonvascular layer of the skin, varying in thickness from 70 to 120 $\mu$m, except on the palms and soles where it may be as thick as 0.8 mm and 1.4 mm, respectively. The epidermis can be further divided into layers, primarily including the stratum corneum (on the outer surface), stratum granulosum, stratum spinosum, and stratum basale (in conjunction with dermis). The dermis consists of a dense bed of vascular connecting tissue, typically varying in thickness from 1 to 2 mm. Although it contains venous plexus in both upper and lower layers, more adipose (i.e., fatty) tissues are found in the lower layer. Major veins are located in subcutaneous tissue.

The effect of samples and media on light will now be discussed briefly. The color of the human skin is affected mostly by the contents of hemoglobin, melanin, and bilirubin, which are the major components in the skin that exhibit significant absorption in the visible and near IR regions of the electromagnetic spectrum. The reddish color of the skin depends to a great extent on the quantity of blood in the subpapillary (upper layer of dermis) venous plexus. The black, yellow, or white skin colors of people originating from different races reflect to a great extent the melanin content located mainly in the lower layers of the epidermis. In the case of patients with cholestasis, an excess amount of bilirubin diglucuronide (a conjugated bilirubin) will appear in blood and tissue in the skin. Another important optical property of the skin is its scattering coefficient. In general, the critical factors that affect the skin's scattering coefficient are the densities, sizes, and shapes of the cells, and the refractive indexes of intercellular fluids and intracellular fluid. The expressions "intercellular fluid", "extracellular fluid", and "interstitial fluid" are used synonymously to mean the fluid in a biological sample that fills spaces between cells of tissues. The epidermis is relatively uniform (though having several layers), and so is the upper dermis, in horizontal directions parallel to the sampling surface (see FIG. 2). However, deeper and deeper into the dermis and subcutaneous tissues, the skin becomes less and less homogeneous as capillaries, veins, various corpuscles, adipose tissues, etc. appear. Then, the effects of refractive index, cell size, and cell shape on the scattering coefficient of the tissue become less important, as the macroscopic structures of the muscles and tissues become more pronounced. In the top layers (e.g., epidermis and upper dermis), the cell sizes and shapes and the refractive indexes of fluids have a significant effect on the scattering coefficient. Analytes that may cause changes in the cell sizes and shapes and the refractive indexes of fluids can be tracked by measuring the scattering coefficient of these layers. For example, any analyte exhibiting significant concentration changes in the intracellular or intercellular fluids can cause the refractive index to change in these fluids. Change in concentration of analytes in the extracellular fluid can also result in changes in the sizes and the shapes of the cells because of osmolality changes in and around the cells. Compounds that may significantly affect these changes in the skin are salts, proteins, fatty acids, sugars (mainly glucose), and water. Also, an increase of the density of cells in blood, i.e., hematocrit, will cause more scattering in the upper dermis layer.

Analytes can be categorized as chromophores, which are molecules that exhibit high absorption in the visible and near-IR spectral range, and nonchromophores, which are molecules that exhibit low absorption in the visible and near-IR spectral range. Chromophores can be determined by the measurement of absorption coefficient. Diffusion theory requires that $\mu_s' >> \mu_a$ in order to assure a multiple scattering condition. Thus, in order to determine a chromophore such as hemoglobin value (or, in turn, hematocrit) only those near-IR wavelengths at which hemoglobin has low absorption must be used. The methods based on the diffusion theory require the use of long pathlength in tissue, which in turn requires a large sampling distance. Large sampling distances usually result in weak signals and poor signal-to-noise ratios.

Non-chromophores exhibit less absorption in visible and near-IR region of the spectrum but may significantly affect the refractive index, and hence, the scattering coefficient of the medium or a sample. Non-chromophores can be determined from the reflectance signal at sampling distances close to the light introduction site. Blood hemoglobin content and hematocrit can be determined from the capillary bed and upper and lower plexus by measuring the intensity of the reflected light at greater sampling distances. This re-emitted light mainly originates from a greater sampling depth, in contrast to the determination of analytes in the epidermis and the top layer of the dermis. Some other analytes that absorb light at short wavelengths in visible region of the spectrum. An example is bilirubin that absorbs at 460 nm. Light penetration depth at these wavelengths can be as shallow as 200 $\mu$m to 250 $\mu$m. Thus, signals detected from a light collection site at a sampling distance close to the light introduction site can be used for a correlation with the concentration of these analytes in the tissue. Therapeutic agents used in photodynamic therapy, such as porphyrin derivatives, absorb light at 600 to 900 nm and could be determined by the method of this invention.

At wavelengths in visible and near-IR region, scattering of the light dominates absorption of the light in biological tissues (i.e., $\mu_s' >> \mu_a$), and photon propagation deviates significantly from Beer's law. One major reason for tissue to scatter light is the existence of mismatch between the indexes of refraction of either the extracellular fluid (ECF) or the intracellular fluid (ICF) and the cellular membranes of the tissue. As used herein, the expression "cellular membranes" encompasses both the cell membrane as well as the membranes of organelles, such as mitochondria or nuclei. Besides undergoing scattering and absorption inside the tissue, photons can be reflected at the tissue/air interface; photons can also be re-emitted from the tissue.

When tissue samples are irradiated at visible and near-infrared wavelengths of light, where the dimension (size) of the scattering material (particles such as cells) is close to the magnitude of the wavelength of light, the reduced scattering coefficient, $\mu_s'$, can be expressed using Mie theory as follows:

$$\mu_s' = 3.28\pi a^2 \rho (2\pi a n_{ex}/\lambda)^{0.37} (m-1)^{2.09} \tag{1}$$

where, $\rho$ represents the volume density, number of particles per unit volume;

a represents the radius of the scattering particle (e.g., cells, mitochondria, or collagen fibrils);

$n_{ex}$ represents the refractive index of the medium (ECF or ICF);

$m = (n_{in}/n_{ex})$, the ratio of the refractive index of the scattering particle $n_{in}$ to the refractive index of the medium $n_{ex}$; and $\lambda$ represents the wavelength of the light. See Graaff, et al., "Reduced light-scattering properties for mixtures of spherical particles: a simple approximation derived from Mie calculations", Applied Optics, Vol. 31, 1992, page 1.

For a given incident wavelength, $\mu_s'$ changes directly with either the cell size, "a", or the refractive index ratio "m", as shown in Equation (1). Because the refractive index of the scattering particles, $n_{in}$, remains relatively constant, $\mu_s'$ is influenced mostly by $n_{ex}$ and particle radius "a". For example, an increase in concentration of glucose, or concentration of other solutes, reduces tissue scattering by decreasing the refractive index difference between the ECF and the cellular membranes. Variations in $n_{ex}$ are not specific for a particular analyte, however, and are affected by any change in the total concentration of solutes in the ECF, including changes in the concentration of glucose, fatty acids, and proteins. The value of $n_{ex}$ is also susceptible to changes in physiological variables, such as temperature and hydration state of the tissue.

Determination of $\mu_a$, $\mu_s$, and g of a tissue at different wavelengths can give information on physical and chemical properties of the tissue, such as concentration of analytes, cell sizes, and tissue heterogeneity. Methods of determining $\mu_{eff}$, $\mu_s'$ and $\mu_a$ are known in the art. One of these methods is the measurement of diffuse reflectance of the skin tissue. In a diffuse reflectance measurement, the measured reflectance is a function of the reduced scattering coefficient $\mu_s'$, the absorption coefficient $\mu_a$, the refractive index of the scattering medium $n_s$, and the refractive index of the surrounding layer $n_o$, which is usually air.

One of the methods of measuring the absorption and scattering coefficients of tissue is referred to as spatially resolved diffuse reflectance, wherein the intensity of re-emitted light is a function of the distance of the light introduction site from the light collection site on the detection surface. In this method, the intensity of the light re-emitted from a sample is measured at several distances on the surface from the site at which light is introduced into the sample. Under certain conditions, intensity of the re-emitted light is related to the separation of the light introduction site from the light collection site by the relationship:

$$R(r) = K_o[\exp(-\mu_{eff} r)]/r \text{ or} \quad (2)$$

$$\text{Log}[r \cdot R(r)] = \text{Log}(K_o) - \mu_{eff} r \quad (3)$$

where, $R(r)$ represents the intensity of light reflected from a sample at a light collection site, which is separated from the light introduction site by a distance r, $K_o$ is a constant, $\mu_{eff}$ is the effective attenuation coefficient, and $\text{Log}(K_o)$ represents the natural logarithm of a number $K_o$.

Separation of $\mu_{eff}$ into absorption and scattering coefficient usually introduces errors in the estimation because of the assumptions used and the statistical nature of the above approach. Thus, quantitation errors of 5% and up to 10% can be encountered in the determination of $\mu_s$ and $\mu_a$ (M. Patterson, et al., "Reflectance as a function of distance, Calculated absorption coefficients and concentrations of PDT dyes in vivo", SPIE Proceedings, Vol. 1065, 1989, pages 115–122, and J. T. Bruulsema, et al. "Correlation between blood glucose concentration in diabetics and non-invasively measured tissue optical scattering coefficients", Optics Letters, Vol. 22, 1997, pages 190–192). If the absorption coefficient of a tissue sample does not fall within the values used in the model assumptions, this approach will lead to erroneous values of the scattering coefficient. These erroneous values may lead to erroneous estimates of the concentrations of analytes determined on the basis of the effect of concentrations on the refractive index of the tissue, and hence the scattering coefficient of the tissue.

The ability to determine $\mu_s'$ and $\mu_a$ separately and accurately depends on the use of diffusion theory approximation and requires a certain ratio of the scattering coefficient to the absorption coefficient ($\mu_s' >> \mu_a$). This requirement limits the wavelength range of the measurement to wavelengths where this relationship holds. Diffusion theory also requires a large separation between the source and the detector, and hence large bodies mass such as skull, the biceps or the calves (U.S. Pat. No. 5,492,118). Diffusion theory is also based on the assumption that human tissue is a homogeneous medium. The structure of the skin is known in the art. Several layers are distinguishable, i.e., the epidermis (including the stratum corneum), the dermis, and subcutaneous tissue. The greater the separation between the source and the detector, the greater the probability of encountering heterogeneous sub-structures such as major blood vessels, muscle fibers and fat tissue.

One way to avoid the limitations of the diffusion theory approximation involves the use of numerical methods, such as the Monte Carlo calculation, to determine the scattering and absorption coefficients, $\mu_s'$ and $\mu_a$. The accuracy of the determined values depends on the inputs to the model, and accounting for layers of skin in such a model is difficult.

The present invention involves methods and apparatus for the measurement of optical properties of tissue taken across a skin boundary, while accounting for the effects of skin layers on the properties measured. The measurement of optical properties of tissue across a skin boundary is adversely affected by the non-homogeneity of the different layers of the skin. Prior art methods and devices ignore the effect of multiple layers of skin tissue on the measured optical properties. Thus, U.S. Pat. Nos. 5,057,695; 5,551, 422; 5,676,143; 5,492,118; 5,419,321; 5,632,273; and 5,513, 642 are silent as to the effect of different layers of skin on optical measurements, and they disclose no methods or apparatus that address this issue. Other prior art methods use widely separated sources of light and detectors of light and a diffusion theory approach to map deep tissue layers. These methods operate on large body masses, such as the skull, thigh, or large arm muscles. Studies of blood circulation in skin show that cutaneous microcirculation occurs at depths of 1 to 2 mm below the skin's epidermal surface (I. M. Braverman, "The Cutaneous microcirculation: ultrastructure and microanatomical organization", Microcirculation, Vol. 4, 1997, pages 329–340). Thus, measurement of optical properties close to the surface of the skin can provide useful information on the effect of blood circulation on the concentration of metabolites in tissues that are close to the surface of the skin. Also, studies of blood circulation close to the surface of the skin by means of laser Doppler flowmetry have shown that laser Doppler flowmetry is a good tool for diagnosing peripheral circulatory disease.

Referring now to FIG. 1, the apparatus of this invention comprises a means for introducing light into tissue at a defined light introduction site. At small distances from the light introduction site are located a plurality of light collection sites, each light collection site being in contact with a light collecting element, which collects the light re-emitted from tissue. The intensity of the re-emitted light collected at this site will be measured by a detector. The source of light for providing light at the light introduction site can be a focused beam of light, a collimated beam of light, or a surface-mounted light emitting diode or a laser diode in contact with the skin. Other sources of light can also be used. In addition, the source of light can be remote from the light introduction site, in which case an optical fiber can be used to carry light from the remote source of light to the light introduction site. The re-emitted light is collected at each of multiple light collection sites located at specific distances, $r_1, r_2, \ldots$, and $r_n$, from the light introduction site. The light collected is directed towards the detector that measures the intensity of the collected light. Re-emitted light can be collected by any of several means. Representative examples of these means of collecting scattered light include, but are not limited to, fibers that are in contact with the skin and a mask with holes at predetermined distances from the light introduction site. The light thus collected can be imaged into a charge coupled device (CCD) camera, a series of photo-diodes in contact with the skin, a one-dimensional or a two-dimensional photodiode array, or any other suitable type of detector.

Although the previous discussion has focused primarily upon a single light introduction site and a plurality of light collection sites comprising light collecting elements, in an alternative embodiment, a plurality of light introduction sites and a single light collection site can be used. A single light collection site replaces the light introduction site, and a plurality of light introduction sites replaces the light collection sites at distances $r_1, r_2, \ldots$, and $r_n$.

The apparatus of the present invention requires that the sites for introducing light and for collecting light be closely spaced. Thus, the apparatus is useful for monitoring analyte effects on the top skin layers, such as epidermis and dermis. The short sampling distances allowed for in this invention are in contrast with those disclosed in the prior art. As an example, Kumar et al. recommend that the separation between the light introduction site and the light collection site be greater than 4 mm, in order to avoid the structural effects of the surface of the skin. See G. Kumar, J. M. Schmitt, "Optical probe geometry for near-infrared spectroscopy of biological tissue", Applied Optics, Vol. 36, 1997, pages 2286–2293.

Another feature of this invention is that it provides a method and apparatus for selecting the optimal distance of separation between the light introduction site and the light collection site for the determination of an analyte. For analytes that significantly affect the scattering properties of the epidermis and the dermis layers by virtue of their effect on the refractive indexes, and hence the scattering coefficients of these layers, their concentrations can be determined at pre-selected short sampling distances. Thus, a distance in the range of 0.4 mm to 1.2 mm is appropriate for such a measurement. For these analytes, such as glucose, one can first generate a calibration relationship between their concentrations determined in vitro and the reflectance signals measured from the epidermis and the upper dermis. One can then use the calibration relationship thus generated to predict the concentrations of the analyte based on subsequent reflectance measurements.

On the other hand, analytes that affect deeper layers in the skin, such as hemoglobin, which is carried by blood flow into the upper and lower plexuses within dermis and subcutaneous tissue, can be determined from measurements at greater sampling distances. Thus, hemoglobin concentration and hematocrit can be better measured at a longer sampling distance, e.g., greater than 1.4 mm. This longer distance corresponds to light re-emitted from skin layers deeper than those encountered for the determination of glucose and other analytes that preferentially affect the optical properties of the upper layers of the skin. This invention offers a tunable sampling distance feature for optimizing analyte detection according to the nature of each analyte.

The properties of skin layers vary from one body part to another and from one individual to another. The difference includes the thickness of each skin layer, pigmentation and hydration state of the skin, tissues in the subcutaneous regions, effects of age and disease condition of the individual on the skin, etc. Thus, the sampling depth and hence the sampling distance at which an analyte should be optimally determined varies by the body part and the individual to be tested.

Other analytes that can be determined by the method and apparatus of this invention include tissue hemoglobin, tissue urea and creatinine, and skin water content. These analytes can be determined individually by selecting the optimal sampling distance for each analyte determination or simultaneously by measuring light re-emitted at multiple sampling distances and correlating each analyte at its optimum sampling distance for maximum correlation with the reference method.

In another aspect, this invention provides a method for the establishment of a calibration relationship for the in vivo measurement of an analyte. A calibration relationship, applicable to a given analyte, a given individual, and a given body part, determines the optimum sampling distance and subsequently the optimum sampling depth in the tissue. It also provides the correlation relationship between the concentration of a given analyte in the sample and the intensity of the re-emitted light detected at the optimum sampling distance. For each analyte and each individual, the method for generating a calibration relationship comprises the steps of:

(1) employing one of the non-invasive methods described herein to make at least one measurement of the concentration of an analyte, by measuring the reflectance of light at each of a plurality of sampling distances, and at substantially the same time, obtain the concentration of the analyte by a standard reference method;

(2) establishing the best achievable correlation relationship between the non-invasive measurement at each of the sampling distances and the concentration of the analyte;

(3) comparing the results obtained at each of the plurality of sampling distances; and (4) selecting the sampling distance that provides the best correlation performance.

To accomplish step (2) above, one usually needs to test multiple mathematical relationships by means of regression methods such as the classical least squares and the principal component regression with respect to their performances. The performances are often measured by parameters such as the correlation coefficient and standard error of estimation in both the calibration process and the validation process. An optimal sampling distance should result in the best performance, as indicated by optimal statistical parameters, such as the highest correlation coefficient and the lowest standard error of estimation. The calibration relationship generated can be used for the subsequent determination of the concentration of the same analyte in the same individual, based only on a non-invasive measurement at a single appropriate sampling distance.

Standard reference methods can be used with this invention in the calibration procedure, so long as they are commonly accepted, in terms of specificity and sensitivity, by medical professionals, i.e., approved by the U.S. Food and Drug Administration, for the specified medical application. For example, commercial clinical chemistry analyzers can be used for determination of the concentrations of total serum bilirubin, blood hemoglobin, and venous blood glucose. The glucose meter commercially available for diabetics' self use can be used to measure glucose concentration in the blood from a few microliters of capillary blood obtained, e.g., by lancing a finger. Microdialysis or other interstitial fluid sampling methods in combination with standard analytical chemistry methods may be used to determine the concentration of glucose in interstitial fluid samples. Hematocrit is commonly determined by centrifugation or cell sorting analyzers for venous blood samples.

FIG. 1 is a schematic diagram showing a light introduction site and several light collection sites located at several sampling distances from the light introduction site. Different tissue layers are probed at different sampling distances. The diffusely reflected light is measured, at each wavelength, for a fixed distance between the light introduction site and the light collection site. This configuration is achieved by using optical fibers in touch with the tissue surface. Selection of distance is achieved by interrogating the light collected at a given fiber at a given distance from the source fiber. This is a stationary illuminating and detecting system. The signal is amplified and is corrected for fluctuation of the light source and variation of the fiber throughput. The corrected signal is used for correlating with the analyte concentration to establish a calibration relationship or for the determination of the analyte.

Alternatively a non-stationary illumination and detection system can be used. The detection distance can be selected by moving the light introduction site on the surface of the sample using a mechanism similar to a compact disk (CD) player read head, to predetermined distances from a light collection site located at a specific site on the surface. Mechanisms for directing a light beam to predetermined distances include beam-stirring devices such as moving mirrors or prisms. The light beam can span a circular or linear path. Another method of achieving the same result involves illuminating a site on the surface of the sample using a stationary fiber in contact with the surface, or illuminating a point on the surface by a collimated or focused beam of light. Re-emitted light is then collected at selected sampling distances on the sample surface by moving a light collecting element on the surface. This can be affected by using a stylus-type (phonograph needle-type) arrangement.

The method of this invention is advantageous over the method disclosed European Patent No. 0 843 986, which does not appreciate the effect of weakly absorbing analytes, including glucose, on the scattering property of tissue layers. This patent does not disclose the method of determining different analytes with the use of different sampling distances, nor does it disclose the method of optimizing the sampling distance to accommodate differences in individuals.

The following non-limiting examples further illustrate this invention.

EXAMPLES

Example 1

Figure 3:
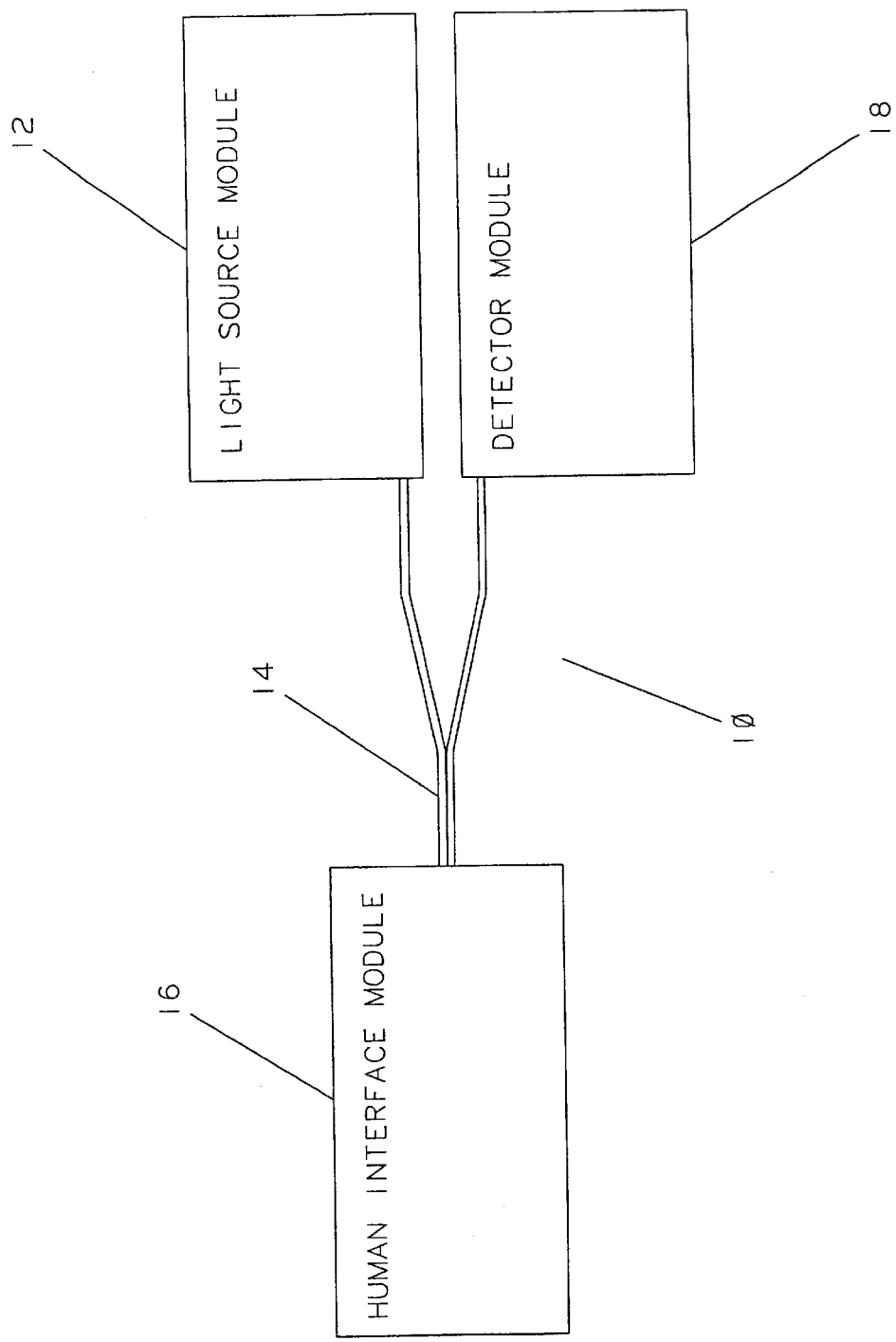
FIG. 3 is a block diagram illustrating a device of this invention.
Figure 4A:
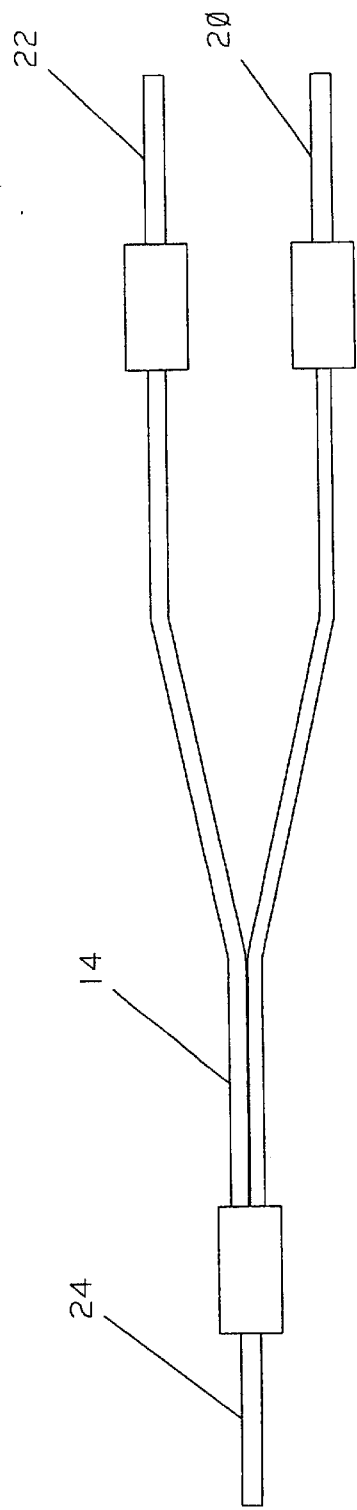
FIG. 4A is a diagram illustrating a bifurcated optical fiber bundle.
Figure 4B:
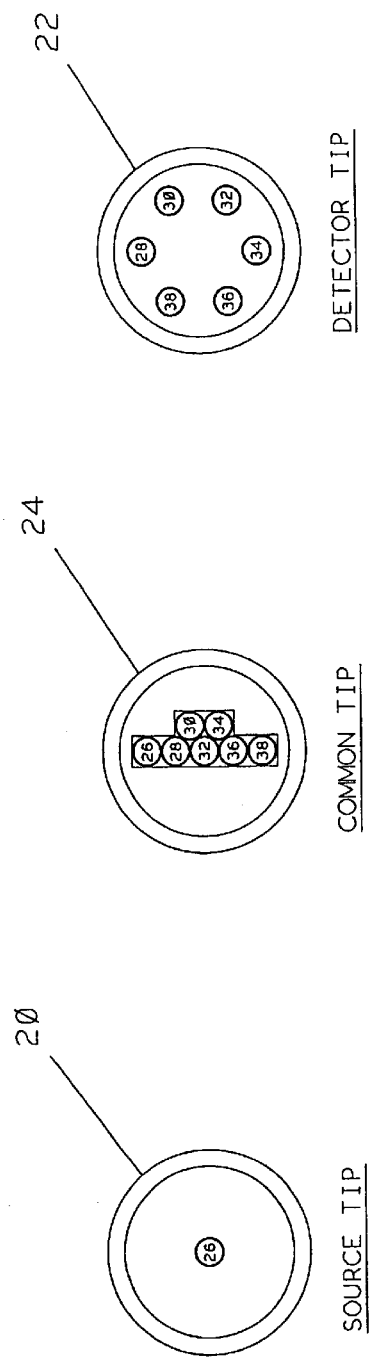
FIG. 4B is a series of diagrams showing portions of the bifurcated optical fiber bundle of FIG. 4A.
Figure 5:
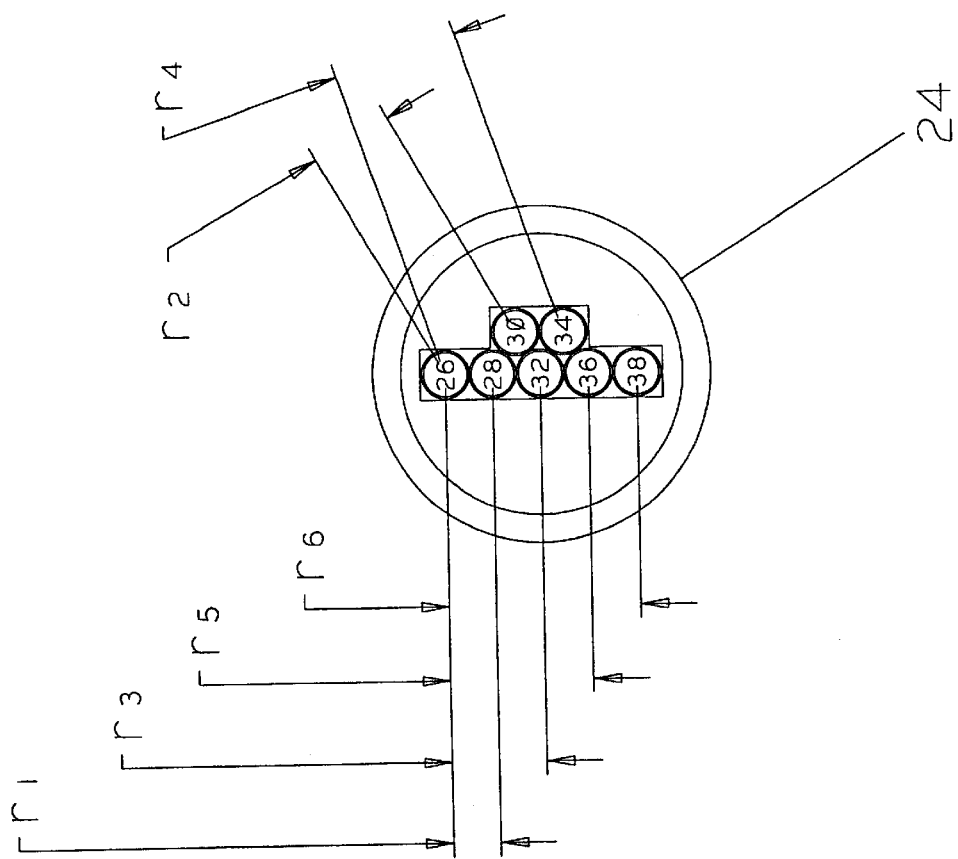
FIG. 5 is a diagram illustrating the nominal separation distances, r, between light collection sites and the light introduction site.

This example shows an apparatus having selectable sampling distances through the use of a plurality of light collection fibers. FIG. 3 through FIG. 5 illustrate an example of an apparatus for the measurement of optical properties, and hence the concentration of different analytes at various depths in tissue. Co-pending U.S. application Ser. No. 09/198,049, filed Nov. 23, 1998 ("Non-invasive sensor capable of determining optical parameters in a sample having multiple layers"), assigned to the assignee of this application, describes in detail many of the components used in the apparatus of this application. The apparatus was intended for introducing light into the skin on forearms of human subjects and measuring the light reemitted therefrom. As shown in FIG. 3, the apparatus comprised a light source module 12, a human interface module 16, a signal detector module 18, and a branched optical fiber bundle 14 that conducted light signals among these three modules. Monochromatic light was generated from the light source module 12 at six wavelengths, i.e., 590 nm, 650 nm, 750 nm, 800 nm, 900 nm and 950 nm. The light was transported to the human interface module 16 through the source fiber 26 in the branched optical fiber bundle 14 (FIG. 4A and 4B). The source fiber 26 received light from its end housed in the source tip 20 in the light source module 12. It emitted the light into the skin of a subject's forearm from its other end, which directly touched the skin at a spot named the light introduction site, housed in the common tip 24 in the human interface module 16. Also touching the skin from the common tip 24, six other fibers 28, 30, 32, 34, 36 and 38 were six independent light collecting elements. Each of these fibers collected light re-emitted from the skin at the spot where it touched the skin, i.e., a light collection site. The human interface module engaged the common tip to the skin. It also provided temperature and pressure control mechanisms for the tip-skin contacting area. The area of skin surrounding the optical element engagement sites was kept at a predetermined constant temperature throughout the measurement. In addition, the human interface module had a comfortable armrest (not shown) for the testing forearm.

Both the source fiber and detection fibers were 400 μm in diameter. The distance from any one detection fiber to the source fiber 26 at the end of the common tip 24 defined the distance between the corresponding light collection site on the skin and the light introduction site also on the skin, i.e., the sampling distances. These distances are indicated in FIG. 5 and listed in TABLE 1.

TABLE 1

| | $r_1$ | $r_2$ | $r_3$ | $r_4$ | $r_5$ | $r_6$ |
| --- | --- | --- | --- | --- | --- | --- |
| Sampling Distance, mm | 0.44 | 0.78 | 0.92 | 1.22 | 1.40 | 1.84 |

The six detection fibers received the re-emitted light from the skin at the common tip 24 and transmitted the light to the detector tip 22 housed in the detector module 18. The ends of all of these fibers at the detector tip 22 were in the focal plane of a lens for the detector (both lens and detector are not shown). However, only when the shutter between a particular fiber end and the detector (not shown) was opened was the light signal from that fiber detected.

Therefore, the sampling depth was determined by selecting a particular light collection fiber and detecting the intensity of re-emitted light collected by this fiber. Selection of a particular light collection fiber was achieved by the use of a programmable shutter that selected one of the six light collection fibers. The shutter was moved by rotating the shutter to a programmed number of steps or a pre-selected detent on its mount.

Example 2

This example illustrates the correlation of non-invasive measurements to hemoglobin concentration or hematocrit. An apparatus as described in FIG. 3 through FIG. 5 was used for the in vivo determination of hemoglobin content and hematocrit for 28 subjects. Some of these subjects were diabetics and some had dark skin.

Tests were conducted on the subjects three hours after their breakfast meal. Non-invasive measurements were performed on the inner part of the subject's left forearm. Silicone oil (Poly(dimethylsiloxane), 200® fluid, viscosity 1,000 cSt, Aldrich Chemical Company) was applied to the skin, and the human interface module 16 with the common tip 24 was placed in contact with the skin. The temperature of the testing site on the skin was allowed to equilibrate at 34° C. for two minutes, and then the measurement was started. Reflected light was collected and reflectance was measured at the six sampling distances as shown in TABLE 1. Wavelengths used in this measurement were 590, 650, 750, 800, 900, and 950 nm.

Venous blood samples of the subjects were obtained immediately following the non-invasive measurement and used for determination of the reference values of hemoglobin concentration and hematocrit. The hematocrit value was determined by a standard micro-centrifuge method (described in C. E. Seiverd, *Hematology for Medical Technologists*, Lea & Febiger, Philadelphia Pa., 1983, pages 320–330). Blood hemoglobin values were determined using a commercial kit and a commercial clinical chemistry analyzer (Vision® Analyzer, Abbott Laboratories, North Chicago, Ill.).

The relative reflectance at detection distance r, R(r) is defined as:

$$R(r) = \frac{I_{reflected}(r)}{I_{incident}} \qquad (4)$$

where, $I_{incident}$ represents the relative intensity of the illuminating light from the source fiber 26 measured from the common tip 24; and, $I_{reflected}(r)$ represents the relative intensity of the re-emitted light from the skin collected by a light collection fiber which has distance r to the source fiber 26 at the common tip 24, and measured at the detector module 18.

Figure 6:
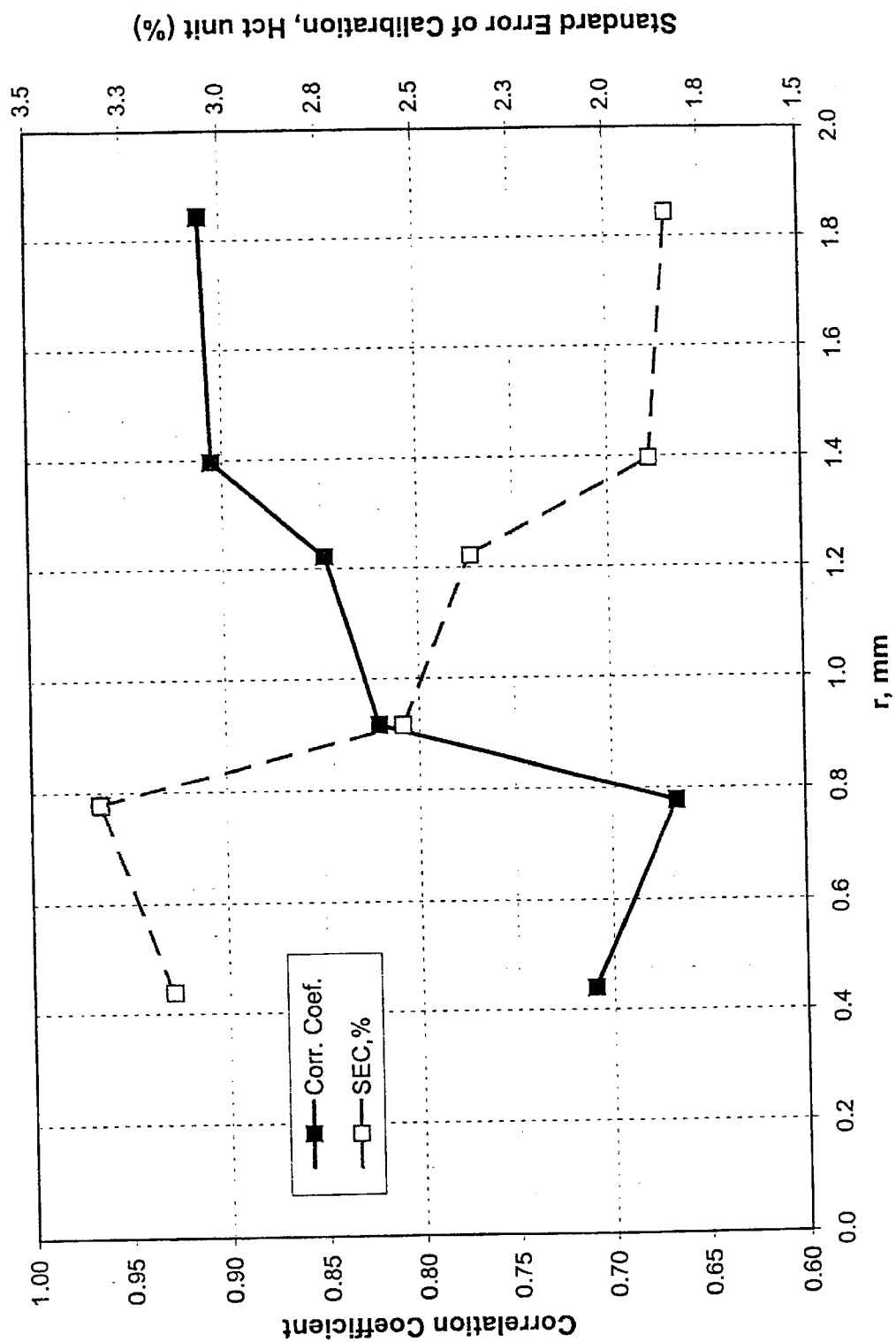
FIG. 6 is an illustration of the correlation coefficient and standard error of calibration for the non-invasive determination of hematocrit as a function of sampling distance.
Figure 7:
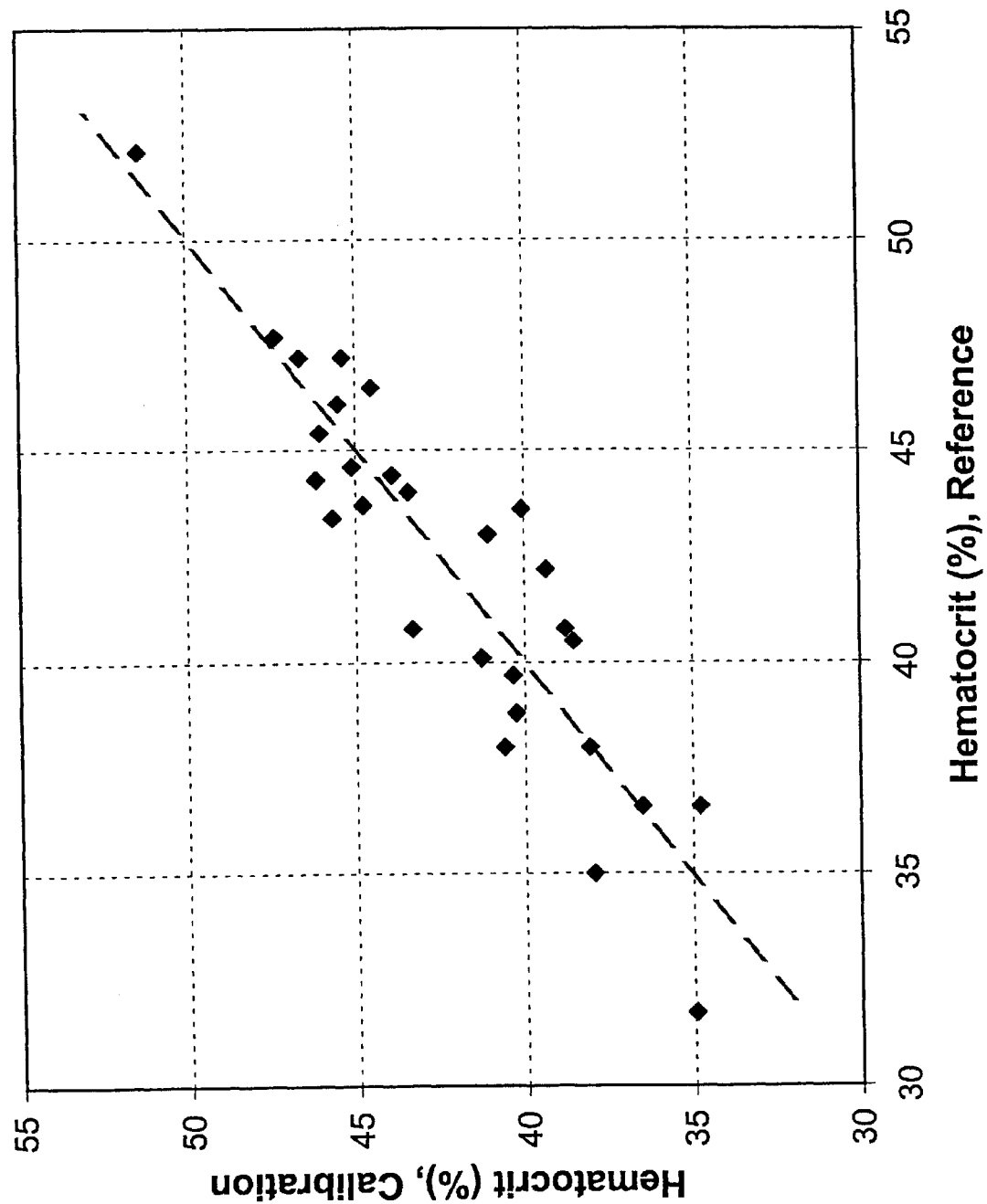
FIG. 7 is a calibration diagram for hematocrit measurement. The sampling distance was 1.84 mm.

Reflectance data at different sampling distances and wavelengths was correlated with the hematocrit and hemoglobin concentrations by means of the linear least square method. For hematocrit, the correlation coefficient was low at the shorter sampling distances (e.g., 0.44 mm and 0.78 mm) and increased significantly at sampling distances greater than about 0.92 mm. The reflectance at a fixed sampling distance of 1.84 mm yielded the highest correlation coefficient and the lowest standard error of calibration for correlation with reference hematocrit values. The correlation coefficient was plotted as a function of sampling distance and the plot is shown in FIG. 6. The correlation coefficient was above 0.9 at distances of 1.40 mm and 1.84 mm. At either of these two distances, the light penetrates through the upper plexus and encounters blood capillaries. The standard error of calibration followed a reverse trend, being greater than 3.2% at the shorter distances and less than 2.0% at the two greater distances. The best regression plot is shown in FIG. 7 and the regression equation is:

$$\text{Hematocrit }(\%)=-0.347-39.0 \cdot \text{Log}[R(590 \text{ nm})]+61.0 \cdot \text{Log}[R(650 \text{ nm})]+151 \cdot \text{Log}[R(900 \text{ nm})]-178 \cdot \text{Log}[R(950 \text{ nm})] \quad (5)$$

where, $\text{Log}[R(\lambda)]$ represents the natural logarithm of reflectance at wavelength $\lambda$(nm) and at a sampling distance of 1.84 mm. The correlation coefficient is 0.911 and the standard error of calibration is 1.84% (hematocrit unit) for the 28 subjects.

A similar correlation was obtained with the use of absorption and scattering coefficients deriving from reflectance values at the all six different sampling distances. This method was described in the prior art (e.g., U.S. Pat. Nos. 5,075,695 and 5,551,422). However, this example demonstrated the correlation with diffuse reflectance data at much shorter sampling distances (instead of greater than 5 mm in the prior art) and using a temperature controlled detection device. The regression equation thus obtained is:

$$\text{Hematocrit }(\%)=55.8+11.4 \cdot \mu_a(590 \text{ nm})-26.1 \cdot \mu_a(650 \text{ nm})-5.72 \cdot \mu_s'(590 \text{ nm})+6.14 \cdot \mu_s'(650 \text{ nm}) \quad (6)$$

The correlation coefficient was 0.87 for the 28 subjects as a group and the standard error of calibration was 2.2% (hematocrit unit).

Thus, the use of reflectance data from a specific sampling depth, collected at a single optimized sampling distance yielded a better correlation and smaller standard error of calibration with respect to the reference values of the hematocrit than does the use of the fitted absorption and scattering coefficient values. Furthermore, the measurement does not require synchronizing to heart beat pulses or a pulsatile signal as taught by U.S. Pat. Nos. 5,499,627 and 5,803,908.

From the plot of the correlation coefficient and the standard error of calibration as a function of sampling distance (FIG. 6), it is apparent that quality of regression is no longer sensitive to the sampling distance when the distances are greater than 1.4 mm.

Skin color was found to affect the calculation that was based on the absorption and scattering coefficients. Thus, it is possible to improve the correlation with hematocrit by eliminating data points corresponding to dark-skinned individuals. In this case the number of light-skinned subjects was 24 and the regression equation becomes:

$$\text{Hematocrit}(\%)=26.2+21.7 \cdot \mu_a(590 \text{ nm})-26.4 \cdot \mu_a(650 \text{ nm})-32.6 \cdot \mu_a(800 \text{ nm})+33.6 \cdot \mu_a(950 \text{ nm}) \quad (7)$$

The correlation coefficient is 0.90 and the standard error of calibration is 1.8% (hematocrit unit).

Effects of skin color were minimized in the correlation to the hematocrit, when the reflectance measured at a single sampling distance and generated from a fixed sampling depth in skin was used. This result is in agreement with the layered structure description of human skin tissue described herein, as at this distance, light penetrates the upper plexus of the dermis layer of the skin and encounters the blood capillaries. Those skilled in the art can use similar analysis and apply this measurement method to other analytes.

Example 3

This example illustrates non-Invasive glucose correlation. The same apparatus as described in Example 1 and a similar setup as described in Example 2 were used for the in vivo determination of glucose for three subjects. For each individual subject, a meal tolerance test protocol was used to induce changes in blood glucose. Correlation between the reflectance measurement and the reference in vitro blood test was carried out.

For each subject, the reflectance measurement was performed repetitively with one set of readings (at six sampling distances as shown in TABLE 1 and at three wavelengths— 590 nm, 800 nm and 950 nm) for every 100 seconds. Tests were conducted under controlled skin temperature of 22° C. Blood samples were taken from the subject by means of a finger-stick every 5 to 15 minutes and tested by means of a commercially available glucose meter. The measurement started when the subject was in a fasting condition. After 10 to 20 minutes, the subject ingested a high sugar drink (commercially available fruit juices, 680-mL liquid and 100 to 120 gram sugars). The total measurement required 90 minutes to 120 minutes.

Figure 8:
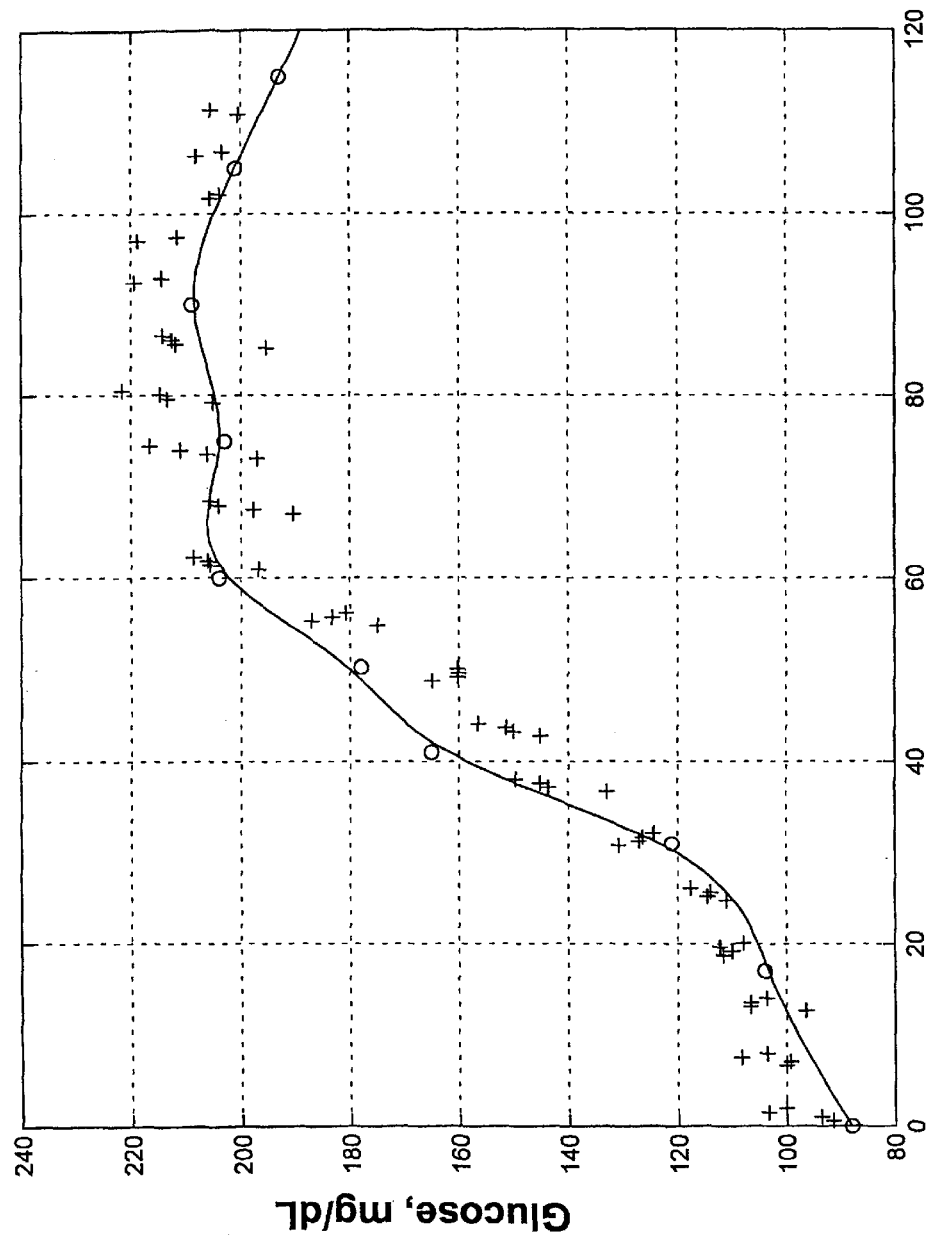
FIG. 8 is a calibration diagram for glucose measurement in a meal tolerance test. The sampling distance was 0.92 mm.

A plot of the glucose values vs. the time during the meal tolerance test on one of the subjects is shown in FIG. 8. The circles represent the result of the reference glucose test using finger-stick capillary blood and a home glucose meter (Glucometer Elite®, Bayer Corp., Elkhart, Ind.). The smooth line passing through these circles shows the fit values of reference glucose concentration resulting from cubic spline smoothing of the finger-stick capillary blood glucose values. Interpolated data points represent the in vitro blood glucose test results at points in time that do not coincide with the points in time at which the tests were actually performed. Classical linear regression was employed to correlate a model comprising reflectance measurement at each single sampling distance at three wavelengths with the fit values of reference glucose concentrations. In most cases, reflectance measurements at $r_3$(r=0.92 mm) at three wavelengths yielded a linear model and fit to the reference glucose values. In FIG. 8, the crosses represent the values of glucose concentration calculated by such a model, i.e., $$\text{Glucose(mg/dL)}=-2898+536 \cdot \text{Log}[R(590 \text{ nm})]-152 \cdot \text{Log}[R(800 \text{ nm})]+2043 \cdot \text{Log}[R(950 \text{ nm})] \quad (8)$$

where, $\text{Log}[R(\lambda)]$ represents the natural logarithm of reflectance at wavelength $\lambda$(nm). The models yielded a correlation coefficient of 0.98 and a standard error of calibration of 8.9 mg/dL.

Figure 9:
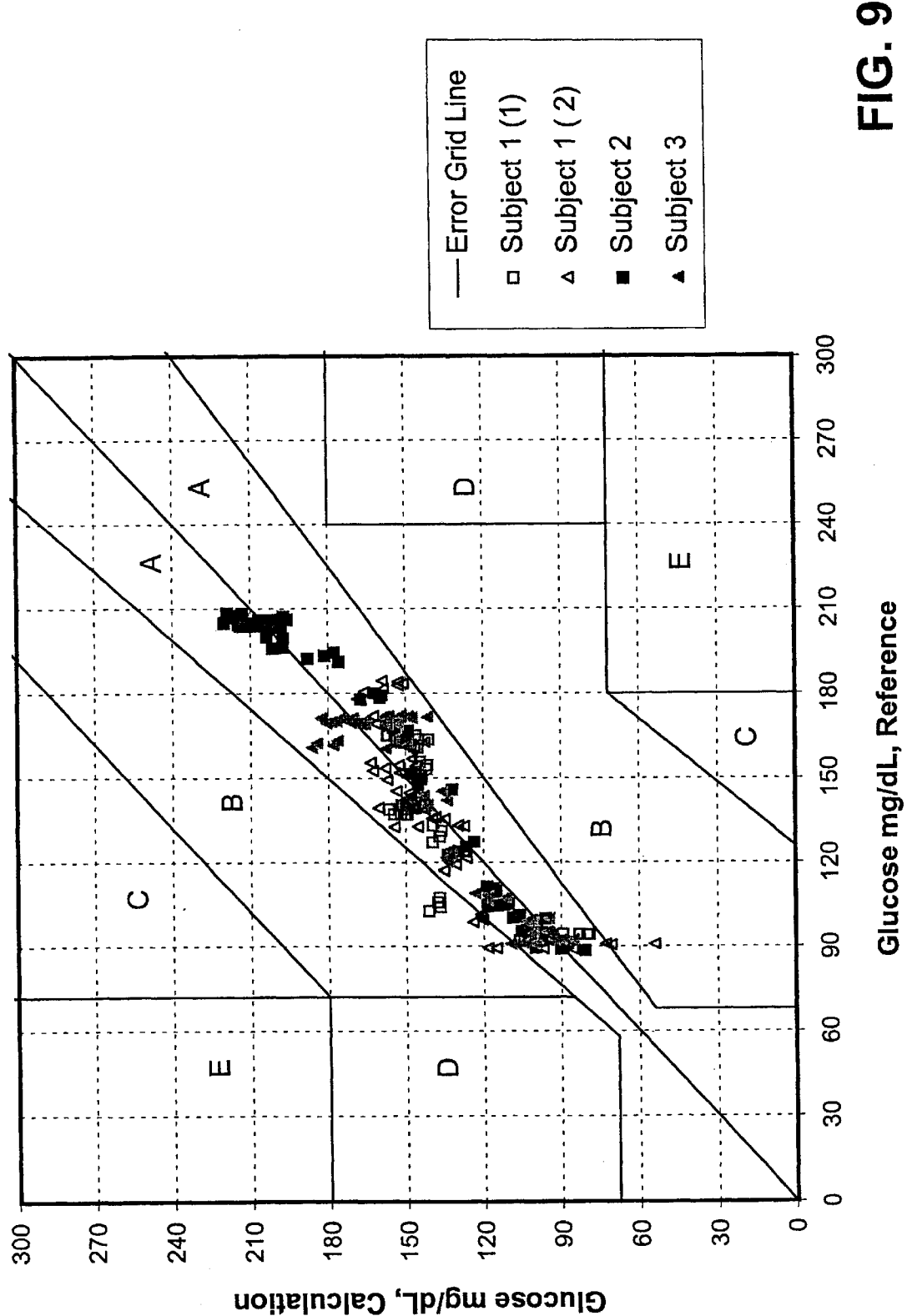
FIG. 9 is a Clark error grid presentation of calibration results in glucose measurement. The sampling distance was 0.92 mm.

Two of the three subjects were non-diabetics, and the third was diagnosed as a diabetic in less than one year. The meal tolerance test was performed on one of the non-diabetic subjects twice in two days. For each of four meal tolerance tests, the reflectance measurement at single distance (0.92 mm) was used to correlate with the reference blood glucose concentration. The calibration results of the four tests are compiled in a Clark error grid presentation, as shown in FIG. 9, where the calculated glucose values are plotted against the reference glucose values. The total number of data points is 250. As seen from the plot, 96% of the data points are in Zone A, the rest are in Zone B, and none is in the zones C, D or E. While data in Zone A and Zone B are considered "acceptable" performance, data in Zones C, D and E may cause serious adverse effects in clinical applications, as they may lead to the wrong types of medical intervention.

Thus reflectance measurement at a single sampling distance that targets the epidermis and the upper dermal layers (sampling distances shorter than 0.92 mm) leads to a good correlation with the concentration of glucose during a meal tolerance test. Such a measurement is simpler than the use of spatially resolved measurement as taught by U.S. Pat. Nos. 5,075,695 and 5,551,442 where signals at multiple sampling distances are needed. Those who are skilled in the art can use some data sets as calibration sets and predict the others using prior art chemometric methods.

Because measurements can be carried out at wavelengths ranging from 400 nm to 2500 nm, the method of this invention avoids the limitations of the method described in EP 0 843 986. In EP 0 843 986, a light beam having a wavelength ranging from 1300 nm to 2500 nm is projected into the skin and the re-emitted light is detected at distances of 0.1–2 mm from the source of light. The spectrum of skin in the 1300–2500 nm range is dominated by water absorption. The path length in the tissue is limited because of strong water absorption. Collecting the signal at the short distances will not allow a significant absorption change due to the weakly absorbing glucose to be measured.

It is important to mention that the determination of hematocrit and hemoglobin (i.e., Example 2), as well as the determination of glucose were performed with the same instrument and the same optical sensor, by programming to use a particular sampling distance for either glucose or hematocrit. One of ordinary skill in the art can configure other distances for other analytes and optimize the measurement for a particular body part that has different thickness of skin layer, a particular individual, or a group of individuals.

Selected distances $r_2$ (0.78 mm) and $r_3$ (0.92 mm) provided the best correlation for glucose determination, depending on testing temperature used. In another set of experiments, selected distance $r_1$ (0.44 mm) provided the best correlation for measurement at 38° C. Thus, distances of less than 1 mm led to a better correlation with the glucose concentrations for the individuals and the body part tested.

At short sampling distances, measurement of signals from shallower sampling depth and with greater contribution from scattering properties yields good correlation with weakly absorbing analytes such as glucose. Glucose would be expected to affect the refractive index of the dermis and the epidermis and change their scattering properties. At large distances from the light introduction site, re-emitted light has greater contribution from absorption and is originated from deeper layers. Blood capillaries distributed in the upper and lower plexus regions of the skin would be expected to affect signals from these regions. Thus, the measurement gives a better correlation with hemoglobin and hematocrit, as demonstrated in Example 2.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the concentration of an analyte in a biological sample, said method comprising the steps of:
    (a) selecting an analyte, the concentration of which analyte is to be determined;
    (b) selecting a single light introduction site from at least one light introduction site and a single light collection site from at least one light collection site on a surface of said biological sample, said single light collection site located at a distance from said single light introduction site, said distance of said single light collection site from said single light introduction site corresponding to a sampling depth in said biological sample, at which sampling depth an optical property of said biological sample is significantly affected by said analyte;
    (c) introducing a beam of light into said biological sample at said single light introduction site;
    (d) collecting the light re-emitted from said biological sample at said single light collection site;
    (e) determining the intensity of said collected light; and
    (f) determining the concentration of said analyte from said intensity of said collected light, wherein the concentration of said analyte is determined by means of a calibration relationship, said calibration relationship relating said intensity of said collected light at said distance of said single light introduction site from said single light collection site to said concentration of said analyte.

2. The method of claim 1, wherein said biological sample has a plurality of layers and said sampling depth corresponds to a layer in said biological sample.

3. The method of claim 1, wherein the intensity of said collected light is determined at a plurality of wavelengths.

4. The method of claim 3, wherein said wavelengths range from about 400 nm to about 2500 nm.

5. The method of claim 3, wherein said wavelengths range from about 400 nm to about 1300 nm.

6. The method of claim 1, wherein said optical property affected by said analyte is scattering of light.

7. The method of claim 1, wherein said optical property affected by said analyte is light absorption.

8. The method of claim 1, wherein said analyte is glucose.

9. The method of claim 1, wherein said analyte is hemoglobin.

10. The method of claim 1, wherein said biological sample is a human tissue.

11. A method for determining the concentrations of a plurality of analytes in a biological sample, said method comprising the steps of:
    (a) selecting at least one analyte of a plurality of analytes, the concentration of which at least one analyte is to be determined;
    (b) selecting a single light introduction site and a single light collection site from a plurality of light collection sites on a surface of said biological sample, said single light collection site located at a distance from said single light introduction site, said distance of said single light collection site from said single light introduction site corresponding to a sampling depth in said biological sample, at which sampling depth an optical property of said biological sample is significantly affected by said at least one analyte of said plurality of analytes;

(c) introducing a beam of light into said biological sample at said single light introduction site;

(d) collecting the light re-emitted from said biological sample at said single light collection site on said surface of said biological sample;

(e) determining the intensity of said collected light;

(f) determining the concentration of said at least one analyte of said plurality of analytes from said intensity of said collected light; and (g) repeating steps (a), (b), (c), (d), (e), and (f) for at least another of said plurality of analytes, wherein the concentrations of said analytes are determined by means of calibration relationships, said calibration relationships relating said intensity of said collected light at said distances of said single light introduction site from said plurality of light collection sites to said concentrations of said analytes.

12. The method of claim 11, wherein said biological sample has a plurality of layers and said sampling depth corresponds to a layer in said biological sample.

13. The method of claim 11, wherein the intensity of said collected light is determined at a plurality of wavelengths.

14. The method of claim 13, wherein said wavelengths range from about 400 nm to about 2500 nm.

15. The method of claim 13, wherein said wavelengths range from about 400 nm to about 1300 nm.

16. The method of claim 11, wherein said optical property affected by said one of said plurality of analytes is scattering of light.

17. The method of claim 11, wherein said optical property affected by said one of said plurality of analytes is light absorption.

18. The method of claim 11, wherein one of said plurality of analytes is glucose.

19. The method of claim 11, wherein one of said plurality of analytes is hemoglobin.

20. The method of claim 11, wherein said biological sample is a human tissue.

21. The method of claim 11, wherein step (f) is carried out subsequent to steps (a), (b), (c), (d), and (e).

22. The method of claim 11, wherein step (f) is carried out simultaneously with steps (a), (b), (c), (d), and (e).

23. A method for determining the concentrations of a plurality of analytes in a biological sample, said method comprising the steps of:

(a) selecting at least one analyte of a plurality of analytes, the concentration of which at least one analyte is to be determined;

(b) selecting a single light introduction site from a plurality of light introduction sites and a single light collection site on a surface of said biological sample, said single light collection site located at a distance from said single light introduction site, said distance of said single light collection site from said single light introduction site corresponding to a sampling depth in said biological sample, at which sampling depth an optical property of said biological sample is significantly affected by said at least one analyte of said plurality of analytes;

(c) introducing light into said biological sample at said single light introduction site;

(d) collecting the light re-emitted from said biological sample at said single light collection site;

(e) determining the intensity of said collected light;

(f) determining the concentration of at least one of said plurality of analytes from said intensity of said collected light; and (g) repeating steps (a), (b), (c), (d), (e), and (f) for at least another of said plurality of analytes, wherein the concentrations of said analytes are determined by means of calibration relationships, said calibration relationships relating said intensity of said collected light at said distance of said single light collection site from said plurality of light introduction site to said concentrations of said analytes.

24. The method of claim 23, wherein said biological sample has a plurality of layers and said sampling depth corresponds to a layer in said biological sample.

25. The method of claim 23, wherein the intensity of said collected light is determined at a plurality of wavelengths.

26. The method of claim 25, wherein said wavelengths range from about 400 nm to about 2500 nm.

27. The method of claim 25, wherein said wavelengths range from about 400 nm to about 1300 nm.

28. The method of claim 23, wherein said optical property affected by said one of said plurality of analytes is scattering of light.

29. The method of claim 23, wherein said optical property affected by said one of said plurality of analytes is light absorption.

30. The method of claim 23, wherein one of said plurality of analytes is glucose.

31. The method of claim 23, wherein one of said plurality of analytes is hemoglobin.

32. The method of claim 23, wherein said biological sample is a human tissue.

33. The method of claim 23, wherein step (f) is carried out subsequent to steps (a), (b), (c), (d), and (e).

34. The method of claim 23, wherein step (f) is carried out simultaneously with steps (a), (b), (c), (d), and (e).

35. A method for generating a calibration relationship for measuring at least one analyte in a biological sample, said method comprising the steps of:

(a) introducing a beam of light into said biological sample at a light introduction site on a surface of said biological sample;

(b) collecting the light re-emitted from said biological sample at each of a plurality of light collection sites on said surface, each of said plurality of light collection sites being at a different sampling distance from said light introduction site;

(c) determining the intensity of said light collected at each of said plurality of light collection sites;

(d) determining a correlation relationship between said intensity of said light collected at each of said plurality of light collection sites with the concentration of said at least one analyte, said concentration determined by an independent reference method;

(e) comparing said correlation relationships for said different sampling distances; and (f) determining an optimal sampling distance for said at least one analyte for subsequent measurement of the concentration of said at least one analyte in a biological sample.

36. The method of claim 35, wherein said at least one analyte is a component of the blood.

37. The method of claim 35, wherein said at least one analyte is a component of interstitial fluid.

38. The method of claim 35, wherein the intensity of said collected light is determined at a plurality of wavelengths.

39. The method of claim 38, wherein said wavelengths range from about 400 nm to about 2500 nm.

40. The method of claim 38, wherein said wavelengths range from about 400 nm to about 1300 nm.

41. The method of claim 38, wherein said optical property affected by said at least one analyte is scattering of light.

42. The method of claim 35, wherein said optical property affected by said at least one analyte is light absorption.

43. The method of claim 35, wherein said at least one analyte is glucose.

44. The method of claim 35, wherein said at least one analyte is hemoglobin.

45. The method of claim 35, wherein said biological sample is a human tissue.

46. A method for generating a calibration relationship for measuring at least one analyte in a biological sample, said method comprising the steps of:

(a) introducing a beam of light into said biological sample at each of a plurality of light introduction sites on a surface of said biological sample;

(b) collecting the light re-emitted from said biological sample at a light collection site on said surface, each of said plurality of light introduction sites being at a different sampling distance from said light collection site;

(c) determining the intensity of said light collected for each of said plurality of light introduction sites;

(d) determining a correlation relationship between said intensity of said light collected for each of said plurality of light introduction sites with the concentration of said at least one analyte, said concentration determined by an independent reference method;

(e) comparing said correlation relationships for said different sampling distances; and (f) determining an optimal sampling distance for said at least one analyte for subsequent measurement of the concentration of said at least one analyte in a biological sample.

47. The method of claim 46, wherein said at least one analyte is a component of the blood.

48. The method of claim 46, wherein said at least one analyte is a component of interstitial fluid.

49. The method of claim 46, wherein the intensity of said collected light is determined at a plurality of wavelengths.

50. The method of claim 49, wherein said wavelengths range from about 400 nm to about 2500 nm.

51. The method of claim 49, wherein said wavelengths range from about 400 nm to about 1300 nm.

52. The method of claim 46, wherein said optical property affected by said at least one analyte is scattering of light.

53. The method of claim 46, wherein said optical property affected by said at least one analyte is light absorption.

54. The method of claim 46, wherein said at least one analyte is glucose.

55. The method of claim 46, wherein said at least one analyte is hemoglobin.

56. The method of claim 46, wherein said biological sample is a human tissue.

57. An apparatus for the determination of the concentration of an analyte in a biological sample, said apparatus comprising:

(a) means for introducing a beam of light into said biological sample at a single light introduction site on a surface of said biological sample;

(b) means for collecting light re-emitted from said biological sample at a single light collection site on said surface located at a predetermined sampling distance from said light introduction site, said predetermined sampling distance corresponding to a sampling depth, at which sampling depth an optical property of said biological sample is significantly affected by said analyte;

(c) means for determining the intensity of said collected light; and (d) means for determining the concentration of said analyte from said intensity of said collect light.

58. The apparatus of claim 57, wherein said means for determining the concentration of said analyte comprises a computer.

59. The apparatus of claim 57, further comprising means for selecting at least one wavelength for said light introduced into said biological sample or said re-emitted light from said biological sample.

60. The apparatus of claim 59, wherein said at least one wavelength is in the 400 nm to 2500 nm range.

61. The apparatus of claim 59, wherein said at least one wavelength is in the 400 nm to 1300 nm range.

62. The apparatus of claim 57, wherein said optical property affected by said analyte is scattering of light.

63. The apparatus of claim 57, wherein said optical property affected by said analyte is light absorption.

64. The apparatus of claim 57, wherein said analyte is glucose.

65. The apparatus of claim 57, wherein said analyte is hemoglobin.

66. The apparatus of claim 57, wherein said biological sample is human tissue.

67. The apparatus of claim 57, wherein said means for introducing a beam of light into said biological sample (a) comprises a single illuminating element and said means for collecting light re-emitted from said biological sample (b) comprises a plurality of light collecting elements.

68. The apparatus of claim 57, wherein said means for introducing a beam of light into said biological sample (a) comprises a plurality of illuminating elements and said means for collecting light re-emitted from said biological sample (b) comprises a single light collecting element.

69. The apparatus of claim 57, wherein said means for introducing a beam of light into said biological sample (a) comprises a single illuminating element capable of moving along the surface of said biological sample.

70. The apparatus of claim 57, wherein said means for collecting light re-emitted from said biological sample (b) comprises a single light collecting element capable of moving along the surface of said biological sample.

* * * * *